United States Patent
Goodwin et al.

(10) Patent No.: US 7,198,947 B2
(45) Date of Patent: *Apr. 3, 2007

(54) PRODUCTION OF FUNCTIONAL PROTEINS: BALANCE OF SHEAR STRESS AND GRAVITY

(75) Inventors: Thomas John Goodwin, Friendswood, TX (US); Timothy Grant Hammond, New Orleans, LA (US); James Howard Kaysen, New Orleans, LA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 11 days.

This patent is subject to a terminal disclaimer.

(21) Appl. No.: 10/734,759

(22) Filed: Dec. 11, 2003

(65) Prior Publication Data

US 2005/0064443 A1 Mar. 24, 2005

Related U.S. Application Data

(60) Continuation of application No. 09/532,001, filed on Mar. 21, 2000, now Pat. No. 6,946,246, which is a division of application No. 09/056,363, filed on Apr. 7, 1998, now Pat. No. 6,730,498.

(60) Provisional application No. 60/043,205, filed on Apr. 8, 1997.

(51) Int. Cl.
*C12N 5/08* (2006.01)

(52) U.S. Cl. ............. 435/369; 435/70.3; 435/70.1; 435/189; 435/325; 435/366; 435/383; 435/403

(58) Field of Classification Search ............ None
See application file for complete search history.

(56) References Cited

U.S. PATENT DOCUMENTS

| | | | |
|---|---|---|---|
| 5,153,131 A | 10/1992 | Wolf et al. | |
| 5,153,132 A | 10/1992 | Goodwin et al. | |
| 5,153,133 A | 10/1992 | Schwarz et al. | |
| 5,155,034 A | 10/1992 | Wolf et al. | |
| 5,155,035 A | 10/1992 | Schwarz et al. | |
| 5,308,764 A | 5/1994 | Goodwin et al. | |
| 5,496,722 A | 3/1996 | Goodwin et al. | |
| 5,627,021 A | 5/1997 | Goodwin et al. | |
| 5,637,477 A | 6/1997 | Spaulding et al. | |
| 5,846,807 A | 12/1998 | Goodwin | |
| 5,851,816 A | 12/1998 | Goodwin et al. | |
| 5,858,783 A | 1/1999 | Goodwin et al. | |
| 5,962,324 A | 10/1999 | O'Conner et al. | |
| 6,117,674 A | 9/2000 | Goodwin et al. | |
| 6,410,320 B1* | 6/2002 | Humes | 435/369 |
| 6,730,498 B1 | 5/2004 | Goodwin et al. | |
| 6,946,246 B1 | 9/2005 | Goodwin et al. | |
| 2003/0064513 A1* | 4/2003 | Uemura et al. | 435/366 |

OTHER PUBLICATIONS

Vats et al, "Stem Cells," Lancet, Aug. 2005, vol. 366, pp. 592-602.*
Poulsom et al, "Adult Stem Cell Plasticity," Journal of Pathology, Jun. 2002, vol. 197, pp. 441-456.*
Anglani et al, "In Search of Adult Renal Stem Cells," Journal of Cellular and Molecular Medicine, 2004, vol. 8, No. 4, pp. 474-487.*
Unsworth et al, "Growing Tissues in Microgravity," Nature Medicine, Aug. 1998, vol. 4, No. 8, pp. 901-907.*
Goodwin et al, "Reduced Shear Stress: A major component in the ability of mammalian tissues to form three-dimensional assemblies in simulated microgravity," Journal of Cellular Biochemistry, 1993, vol. 51, pp. 301-311.*
Hammond et al, "Optimized suspension culture: the rotating-wall vessel," American Journal of Physiology Renal Physiology, 2001, vol. 281, pp. F12-F25.*
Goodwin et al., Rotating-Wall vessel coculture of small intestine as a prelude to tissue modeling: aspects of simulated microgravity, Feb. 1993,proc Soc Exp Biol Med, vol. 202, pp. 181-192.
Condamine et al., Local action of phosphate depletion and insulin-like growth factor 1 on in vitro production of 1, 25-dihydroxyvitamin D by cultured mammalian kidney cells, Oct. 1994, American Society for Clinical investigation, vol. 94, pp. 1673-1679.
Hough et al., Vitamin D. Metabolism in the chronic streptozotocin-Induced diabetic rat., 1983, Endocrinology, vol. 113, pp. 790-796.
Jessup et al., Prospects for Use of Microgravity-Based Bioreactors to Study Three-Dimensional Host-Tumor Interactions in Human Neoplasia, Journal of Cellular Biochemistry, 52:290-300, 1993.
Spaulding et al., Advances in Cellular Construction, Journal of Cellular Biochemistry, 51:249-251, 1993.
Deluca, New Concepts of Vitamin D Functions, Annals New York Academy of Sciences; 669:59-69, 1992.
Hammond et al., Analysis and Isolation of renal tubular cells by flow cytometry, Kidney International, 42:997-1005, 1992.
Hammond et al., Forward Scatter Width Signals Resolve Multiple Populations of Endosomesm, Cytometry, 14:411-420, 1993.
Wolf et al., Analysis of Gravity-Induced Particle Motion and Fluid Perfusion Flow in the NASA-Designed Rotating Zero-Head-Space Tissue Culture Vessel, NASA Technical Paper 3143.
Moestrup et al., The Intrinsic Factor-Vitamin B12 Receptor and Target of Teratogenic Antibodies Is a Megalin-binding Peripheral Membrane Protein with Homology to Development Proteins, Journal of Biological Chemistry, 273:5235-5242, 1998.

* cited by examiner

*Primary Examiner*—Leon B. Lankford, Jr.
*Assistant Examiner*—Allison M. Ford
(74) *Attorney, Agent, or Firm*—Kurt G. Hammerle

(57) ABSTRACT

The present invention provides a method for production of functional proteins including hormones by renal cells in a three dimensional co-culture process responsive to shear stress using a rotating wall vessel. Natural mixture of renal cells expresses the enzyme 1-a-hydroxylase which can be used to generate the active form of vitamin D: 1,25-diOH vitamin D3. The fibroblast cultures and co-culture of renal cortical cells express the gene for erythropoietin and secrete erythropoietin into the culture supernatant. Other shear stress response genes are also modulated by shear stress, such as toxin receptors megalin and cubulin (gp280). Also provided is a method of treating in-need individual with the functional proteins produced in a three dimensional co-culture process responsive to shear stress using a rotating wall vessel.

7 Claims, 17 Drawing Sheets

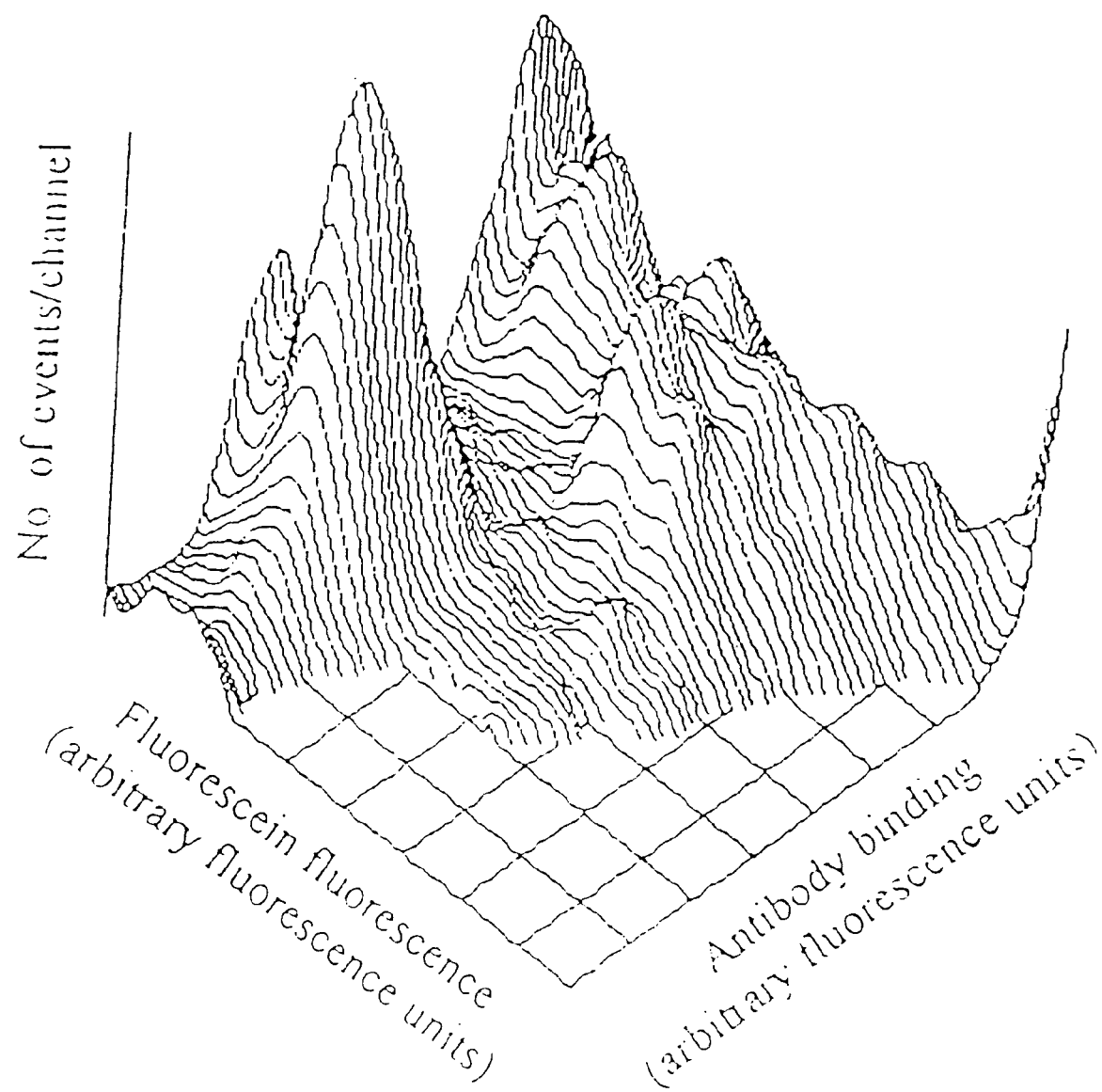
FIGURE 2A (cont.-1)

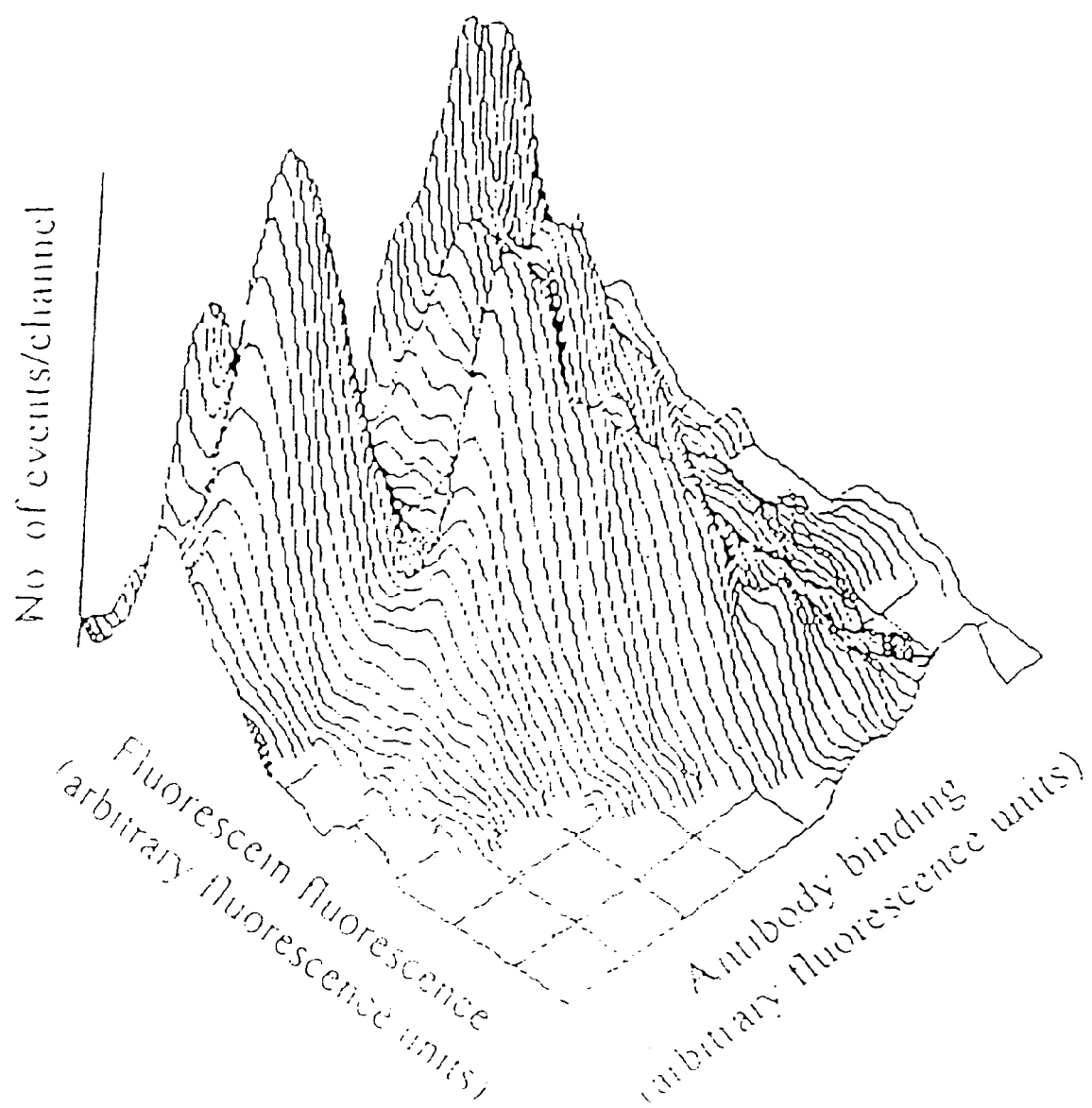
FIGURE 2A (cont.-2)

Band B control    STLV

―

Band D control    STLV

FIGURE 3B

|       | ICAM | MnSOD  |
|-------|------|--------|
| NT    | 1485 | 11876  |
| C 40  | 1977 | 7748   |
| C80   | 6178 | 10881  |
| AS 40 | 2856 | 5902   |
| AS80  | 2604 | 5116.7 |

|       | MnSOD  |
|-------|--------|
| NT    | 11876  |
| C 40  | 7748   |
| C80   | 10881  |
| AS 40 | 5902   |
| AS80  | 5116.7 |

8 Day Bag Control

8 Day STLV

PRODUCTION OF FUNCTIONAL PROTEINS: BALANCE OF SHEAR STRESS AND GRAVITY

RELATED APPLICATIONS

The present application is a continuation of U.S. application Ser. No. 09/532,001, filed Mar. 21, 2000, now U.S. Pat. No. 6,946,246, which is a divisional of U.S. application Ser. No. 09/056,363, filed Apr. 7, 1998, now U.S. Pat. No. 6,730,498, which claims the benefit of provisional U.S. Application Ser. No. 60/043,205, filed Apr. 8, 1997.

FEDERAL FUNDING NOTICE

The present invention was funded by NIH Grant DK46117, NIH R21, and NASA NRA Grant 9-811. Consequently, the United States government has certain rights in this invention.

The jointly made invention described herein was made by an employee of the United States Government and may be manufactured and used by or for the Government of the United States of America for governmental purposes without the payment of any royalties hereon or therefor.

The invention described herein was also made by inventors in the performance of work under an agreement with Tulane Educational Fund and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates generally to the fields of protein chemistry, endocrinology and gene therapy. More specifically, the present invention relates to a method for production of functional proteins in culture in response to shear stress using a rotating wall vessel.

2. Description of the Related Art

A successful and documented modality to induce polarization and differentiation of cells in culture is the rotating wall vessel (1–4). In rotating wall vessels gravity is balanced by equal and opposite physical forces including shear stresses. In engineering terms this has been claimed to simulated microgravity at boundary conditions [Wolf D. A. and R. P. Schwarz. (1991) NASA Technical Paper 3143].

Rotating wall vessels, including models with perfusion, are a quantum advance. The rotating wall vessel is a horizontally rotated cylindrical cell culture device With a coaxial tubular oxygenator (1, 5–7). The rotating wall vessel induces expression of select tissue-specific proteins in diverse cell cultures (1–2, 8–9). Examples of expression of tissue-specific proteins include carcinoembryonic antigen expression in MIP-101 colon carcinoma cells (2), prostate specific antigen induction in human prostate fibroblasts (7), through matrix material induction during chondrocyte culture (8). The quiescent cell culture environment of the rotating wall vessel balances gravity with shear and other forces without obvious mass transfer tradeoff (1–2, 4). The rotating wall vessel provides a culture environment suitable for co-cultures of diverse cell types, and three dimensional tissue construct formation.

Rotating wall vessel technology is being used in clinical medical practice recently by facilitating pancreatic islet implantation (4, 10). Pancreatic islets are prepared in rotating wall vessels to maintain production and regulation of insulin secretion. The islets are alginate encapsulated to create a non-inflammatory immune haven, and are implanted into the peritoneal cavity of Type I diabetic patients. This implantation of pancreatic islets has maintained normoglycemia for 18 months in diabetic patients, and progressed to Phase III clinical trials (4, 10). These vessels have also been applied to, for example, mammalian skeletal muscle tissue, cartilage, salivary glands, ovarian tumor cells, and colon crypt cells (11–13). Previous studies on shear stress response in endothelial cells, and rotating wall vessel culture have been limited to structural genes (14–16). These studies did not address the issue of a process for the production of functional molecules, such as hormones. Shear stress response elements have not previously been demonstrated in epithelial cells, either for structural genes of production of functional molecules.

Vitamin D dependent rickets has been a disease familiar to family farms and larger animal husbandry industries for centuries (17–18). The development of renal replacement therapy by dialysis in humans expanded vitamin D deficient bone disease from an occasional human clinical caveat to a common clinical problem. This led to identification of the active form of vitamin D as 1,25-diOH $D_3$ and the development of a multi-billion dollar per year worldwide market, predominantly in end-stage renal disease patients, to provide replacement hormone clinically (18). The active 1,25-diOH form of vitamin $D_3$ is mainly used to treat bone disease in dialysis patients but has *also been implicated as a therapy for osteoporosis, and some forms of cancer. Recently, the effects of vitamin D have been recognized to play a central role not only in other common bone lesions such as osteoporosis due to aging and steroid induced osteoporosis, but in immune function and surveillance, growth and development, and cardiac and skeletal muscle function (19–22).

Several-active forms of vitamin D have been identified, vitamin D receptors cloned, and nuclear binding proteins for the hormone identified and cloned (17–22). Studies on the regulation of 1α-hydroxylase activity are limited by the lack of a renal cell line with regulated expression of the enzyme. The only reports of 1-α-hydroxylase activity in culture utilize freshly isolated chicken renal cortical cells in which the activity declines precipitously within 48 hours of plating in culture (28).

The importance of the renal 1-α-hydroxylase is best understood by comparing the kinetics of the renal enzyme to other forms in the body (29–30). Demonstration that nephrectomy in pregnant rats did not completely abolish 1,25-diOH-$D_3$ formation sparked an intensive search for extrarenal sites of 1 α-hydroxylase activity (29). Although 1 α-hydroxylase activity has been reported in monocytes, liver, aortic endothelium and a variety of placental and fetal tissues, the enzyme kinetics contrast sharply with the renal 1 α-hydroxylase. Extrarenal 1-α-hydroxylase has a much higher Km indicating that much higher substrate levels are needed for activity (29). In the uremic patient, extrarenal 1,25-diOH $D_3$ production is very limited due to a relative lack of substrate. Administrating large quantities of 25-OH $D_3$ substrate to anephric patients modestly boosts plasma 1,25-diOH $D_3$ levels (29).

The lack of a differentiated polarized line of renal tubular epithelial cells for investigative purposes persists despite extensive searches by several laboratories (31–38). Renally derived cell lines transformed with viruses or tumor cells to produce immortality continue as some of the most popular cell biological tools to study polarized delivery (31, 33, 35). But these renally derived immortal cell lines such as MDCK or LLP-CK1 retain few if any of the differentiated features characteristic of renal epithelial cells. Similarly, primary cultures rapidly dedifferentiate and modalities as diverse as basement membrane matrices, growth supplements or Millipore inserts achieve only modest degrees of polarity (37–38).

The pathognomonic structural features of renal proximal tubular epithelial cells are the abundance of apically derived microvilli, the glycoprotein content of associated intermicrovillar clefts, and the highly distinctive arrangement of subapical endosomal elements (39–40). Renal epithelial cells of the proximal tubule are characterized by thousands of long apical microvilli. The apical endosomal machinery begins in intermicrovillar clefts. The endosomal pathway is characterized by clathrin coated vesicles, small spherical endosomal vesicles, with deeper larger endosomal vacuoles (33, 39). From the endosomal vacuoles proteins and lipids either recycle to apical surface in dense apical tubules or shuttle to lysosomes to be degraded.

A cluster of apical proteins with homologous sequence repeats are especially desirable to express in cultured cells as they are thought to be molecular mediators of renal injury (41–43). Two of these proteins megalin (gp330) and cubulin (gp280) (Moestrup, et al., *J. Biol. Chem.* β273 (9):5325–5242 (1998) are molecular mediators of tubular vacuolation and ensuing secondary damage. Megalin (gp330) is a receptor found on the luminal surface of the proximal tubular cells of the kidney. Megalin binds several proteins and drugs including aminoglycoside antibiotics and other polybasic drugs. Megalin is expressed in the kidney, lung, testes, ear, and placenta. The only cells which express megalin in culture are immortalized placental cells. There is no known renal cell culture which expresses megalin. Gp280 is a receptor found on the luminal surface of the proximal tubular cells of the kidney. Gp280 binds several proteins and drugs including intrinsic factor-cobalamin (vitamin B12 bound to its carrier protein) and myeloma light chains. Cubulin (gp280) is expressed in the kidney, ear, and placenta. The only cells which express cubulin (gp280) in culture are immortalized placental cells. There is no known renal cell culture which expresses cubulin (gp280).

Erythropoietin (EPO) is a hormone produced in the kidney, and secreted into the blood. Erythropoietin controls the rate of production of red blood cells by the bone marrow. Erythropoietin may be produced by the interstitial cells between the tubules or the proximal tubular cells or both. Erythropoietin production is lost in all known renal cell culture systems. Erythropoietin is mainly used to treat anemia in dialysis patients but is also popular to treat the anemia of AIDS patients and many forms of cancer.

The prior art is deficient in the lack of effective means of producing functional proteins including hormones in response to shear stress. Further, the prior art is deficient in the identification of shear stress response elements in epithelial cell genes. The present invention fulfills this longstanding need and desire in the art.

SUMMARY OF THE INVENTION

In one embodiment of the present invention, there is provided a method of producing a functional protein, comprising the steps of: isolating mammalian cells; placing said cells into a rotating wall vessel containing a cell culture comprising culture media and culture matrix; producing three-dimensional cell aggregates under simulated microgravity conditions; and detecting expression of the functional protein in the cell culture.

In another embodiment of the present invention, there is provided a method of inducing expression of at least one gene in a cell, comprising the steps of: contacting said cell with an transcription factor decoy oligonucleotide sequence directed against a nucleotide sequence encoding a shear stress response element; and determining the expression of said gene in said cell.

In yet another embodiment of the present invention, there is provided a transcription factor decoy, comprising an oligonucleotide sequence directed against a nucleotide sequence encoding a shear stress response element.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted however, that the appended drawings illustrate preferred embodiments of the invention and therefore are not to be considered limiting in their scope.

FIG. 1 shows homogeneity and structure of human renal epithelial cells in culture. Flow cytometry frequency histograms demonstrate number of cells positive for the proximal tubular marker γ-glutanyl transferase.

FIG. 2 shows protein expression in the rotating wall vessel.

FIG. 3 shows gene expression in the rotating wall vessel. FIG. 3A and FIG. 3B show differential display of genetic expression of rat renal cortical cells grown in conventional culture or rotating wall vessels. Differential display of expressed genes was compared in aliquots of the same cells grown in a 55 ml rotating wall vessel (STLV) or conventional gas permeable 2-dimensional bag controls. For differential display, copies of expressed genes were generated by polymerase chain reaction using random 25 mer primers and separated on a 6% DNA sequencing gel (FIG. 3A). Bands of different intensity between control and STLV, representing differentially expressed genes, were identified by visual inspection, excised and reamplified using the same primers. Differential expression and transcript size were confirmed by Northern hybridization (FIG. 3B). PCR products were then subcloned into the pGEM-T vector and sequenced. Sequences were compared to the Genebank sequences using the BLAST search engine. One expressed gene which decreased in the STLV (band D on gelabove) was identified as rat manganese-containing superoxide dysmutase (98% match 142 of 144 nucleotides). Two genes which increased in the STLV, band A was identified as the interleukin-1 beta gene (100% match for 32 of 32 nucleotides) and B and B which corresponded to a 20 kB transcript on a Northern blot appears to be a unidentified gene that has a 76% homology to the mouse GABA transporter gene.

FIG. 4 shows structure and effects of antisense probe for shear stress response element on rat renal cortical epithelial cells.

DETAILED DESCRIPTION OF THE INVENTION

Figure 1A:
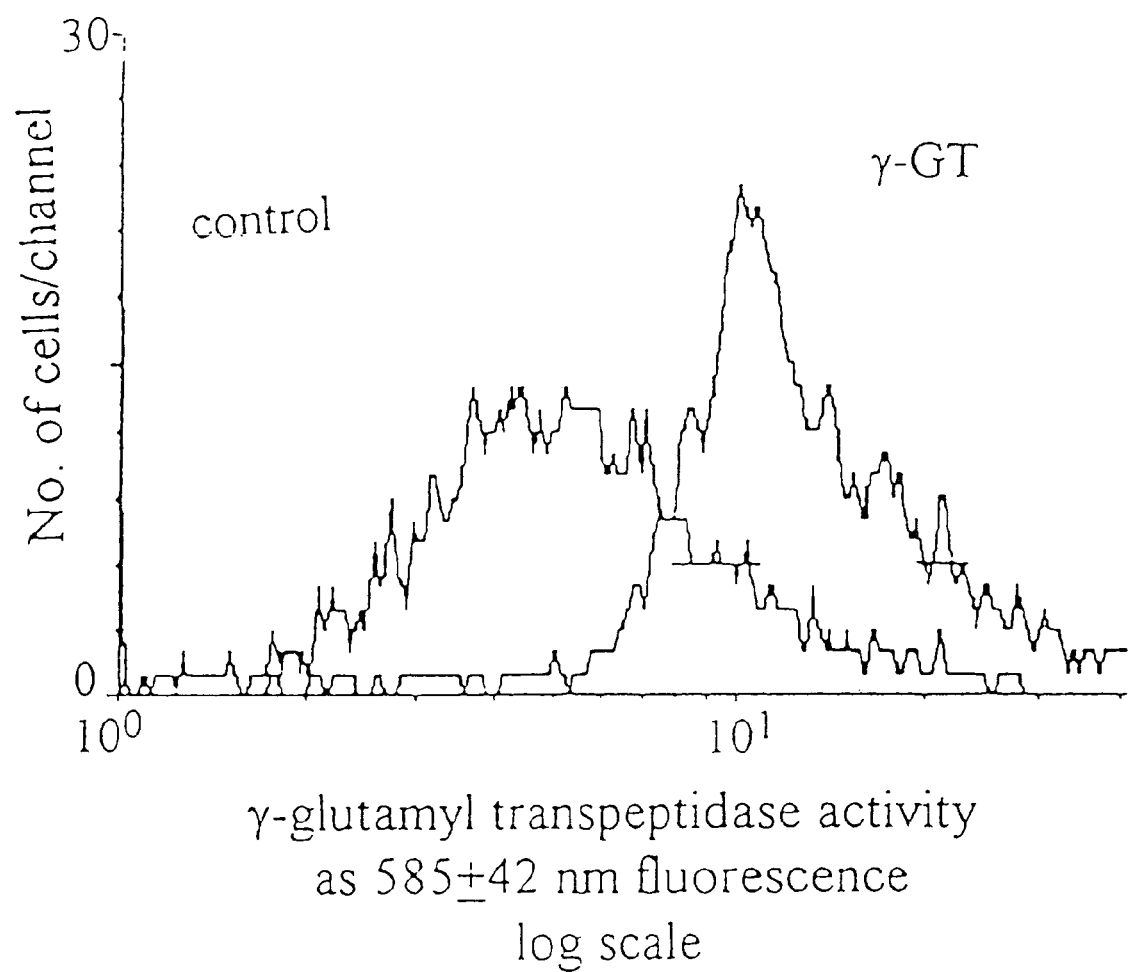
FIG. 1A shows the number of cells with y-glutamyl transferase activity as the frequency of activity in 2000 cells compared to an unstained control with trapping agent alone. This is the raw digest of human renal cells.

The present invention is directed to a method of producing a functional protein, comprising the steps of: isolating mammalian cells; placing said cells into a rotating wall vessel containing a cell culture comprising culture media and culture matrix; producing three-dimensional cell aggregates under simulated microgravity conditions; and detecting expression of the functional protein in the cell culture. Generally, simulated microgravity conditions comprise a balance between gravity and oppositely directed physical forces. Representative examples of such physical forces include sedimentational shear stress, centrifugal forces, viscosity and Coriolis forces.

Preferably, the functional protein is selected from the group consisting of a hormone, a toxin receptor and a shear stress dependent functional biomolecule. Representative examples of hormones which can be produced according to the method of the present invention include 1,25-dihydroxy-vitamin D3 and erythropoietin. Representative examples of toxin receptors which can be produced according to the method of the present invention include megalin and cubulin. Representative examples of shear stress dependent functional biomolecule which can be produced according to the method of the present invention include is selected from the group consisting of villin, magnesium dependent superoxide dismutase, nitric oxide synthase, c-fos, c-jun, platelet derived growth factor-b, transforming growth factor-b, tissue-type plasminogen activator and monocyte chemotactic protein-1, megalin, cubulin, erythropoietin and 1-a-hydroxylase.

Generally, any mammalian cell could be used in the methods of the present invention. Representative examples of mammalian cells include renal cortical cells, renal fibroblast cells, hepatocytes, pancreatic islets, renal interstitial cells, parathyroid cells, thyroid cells, pituitary cells, ovarian cells and testicular cells. Generally, the cell is selected from the group consisting of epithelial cell and endothelial cell. Preferably, the cell contains shear stress response elements.

Representative examples of shear stress response elements include GAGACC and GGTCTC.

In the methods of the present invention, the rotating wall vessel is initiated and maintained from about 6 rotations per minute to about 16 rotations per minute. Preferably, the sedimentational shear stress is from about 0.2 dynes/cm2 to about 1.0 dynes/cm2. The culture matrix may contain a core structure selected from the group consisting of cell aggregates and microcarrier beads, although other components to such a culture matrix are well known to those having ordinary skill in this art.

The present invention is also directed to a method of inducing expression of at least one gene in a cell, comprising the steps of: contacting said cell with an transcription factor decoy oligonucleotide sequence directed against a nucleotide sequence encoding a shear stress response element; and detennining the expression of said gene in said cell. Generally, oligonucleotide comprises a terminal phosphothiorate moiety and a phosphodiester backbone and a structure which allows the oligonucleotide to pass cell membranes and accumulate in the nuclear compartment of the cell. Generally, the cell is a cultured cell. Preferably, the cell is selected from the group consisting of an epithelial cell and an endothelial cell. Representative examples of which can be used in this method include renal cortical cell, renal fibroblast cell, hepatocyte, pancreatic islet, renal interstitial cell, parathyroid cell, thyroid cell, pituitary cell, ovarian cell and testicular cell. In one embodiment, the cell is grown in two dimensional culture. Representative examples of shear stress response elements include GAGACC and GGTCTC. Preferably, the gene encodes a protein selected from the group consisting of megalin, cubulin, erythropoietin and 1-a-hydroxylase. The concentration of the oligonucleotide useful in this method generally ranges from about 10 nM to about 10 mM.

The present invention is also directed to a transcription factor decoy, comprising an oligonucleotide sequence directed against a nucleotide sequence encoding a shear stress response element. Preferably, the nucleotide sequence encoding a shear stress response element has a sequence selected from the group consisting of GAGACC and GGTCTC.

In one preferred technique, the rotating wall vessel is generally initiated and maintained at 10 rotations per minute. Preferably, the rotating wall vessel provides a balance of forces comprising gravity and equal and opposite sedimentational shear stress. Useful sedimentational shear stress rates within the context of the claimed methods are from about 0.2 dynes/cm2 to 1.0 dynes/cm2.

As used herein, rotating wall vessels refers to a cylindrical horizontal rotating culture vessel with a coaxial oxygenator.

As used herein, shear stress response elementll refers to a sequence of a family of genes in the cell nucleus which binds one or more transcription factors in response to shear stress on the cell. A representative example of a shear stress response element is GAGACC or its complementary sequence GGTCTC.

As used herein, shear stress conditions refers to flow of liquid, or current of liquid over cells which causes genes to turn on or off.

As used herein, slow turning lateral vessel (STLV) refers to one specific size and shape of a rotating wall vessel.

As used herein, differential displayll refers to displaying on a filter, gel or chip a discrete set of genes turned on or off in a cell under two different conditions.

As used herein, simulated microgravityll refers to balance of gravity by oppositely directed forces including shear stresses during rotational wall vessel culture.

As used herein, graded gravitational sedimentation shear refers to the shear imparted to a particle or cell falling through fluid.

As used herein, functional protein refers to a protein with biological effects.

As used herein, three-dimensional co-culture processll refers to cells grown in a matrix or on beads (or other three-dimensional structural support) in a three-dimensional array, rather than on a flat plate.

As used herein, Coriolis forcell refers to an incidental flow field caused by the rotating gravity vector in the rotating wall vessel.

As used herein, shear stress refers to the force felt at the surface of the particle as it moves through the fluid.

As used herein, gravity induced sedimentation refers to the force on a particle in the rotating wall vessel making it fall through the fluid due to gravity.

As used herein, centrifugal force refers to the force on a particle in the rotating wall vessel which pulls it towards the wall due to rotational speed.

As used herein, transcription factor decoy refers to an oligonucleotide folded to form a double stranded DNA which binds a nuclear transcription factor. The transcription factor decoy prevents the transcription factor from binding promoter regions regulating expression of specific genes.

The following examples are given for the purpose of illustrating various embodiments of the invention and are not meant to limit the present invention in any fashion.

EXAMPLE 1

Human Renal Cortical Cells

Human renal cortical cells were isolated by Clonetics Inc. (San Diego, Calif.) from kidneys unsuitable for transplantation. Differential trypsinization resulted in cell fractions highly purified for proximal tubular cells compared to the natural mixture of cells in the renal cortex. The co-culture of the natural cell mix, and highly purified proximal tubular cells were cultured separately in a special growth medium with 2% fetal calf serum.

EXAMPLE 2

Rat Renal Cortical Cells

Rat renal cells were isolated from renal cortex harvested from euthenized Sprague Dawley rats (Harlan Sprague-Dawley, Cleveland Ohio) as described (44). In brief, renal cortex was dissected out with scissors, minced finely in a renal cell buffer 137 mmol NaCl, 5.4 mmol KCl, 2.8 mmol CaCl2, 1.2 mmol MgCl2, 10 mmol HEPES-Tris, pH 7.4. The minced tissue was placed in 10 ml of a solution of 0.1% Type IV collagenase and 0.1% trypsin in normal saline. The solution was incubated in a 37° C. shaking water bath for 45 minutes with intermittent titration. The cells were spun gently (800 rpm for 5 minutes), the supernatant aspirated, the cells resuspended in 5 ml renal cell buffer with 0.1% bovine serum, and passed through a fine (70 mm) mesh. The fraction passing through the mesh was layered over a discontinuous gradient of 5% bovine serum albumin and spun gently. The supernatant was again discarded. The cells were resuspended in DMEM/F-12 medium (ciprofloxacin and fungizone treated) and placed into culture in various culture vessels in a 5% CO2 95% O2 incubator.

EXAMPLE 3

Culture Techniques: Rotating Wall Vessels

When grown under conventional conditions in DMEM/F12 supplemented with fetal calf serum and an antibiotic cocktail such as ciprofloxacin and fungizone, both the highly purified cells as well as the cell mix form a monolayer. Fetal calf serum was used at optimal concentration: 2% for human calls and 10% for rat cells. In order to increase epithelial cell differentiation (1, 45), renal cells were cultured in a rotating wall vessels known as a 55 ml slow turning lateral vessel (STLV) (1, 45). To initiate cell culture, the slow turning lateral vessel was filled with medium, and seeded by addition of cell suspension (2×106 cells/ml). Residual air was removed through a syringe port and vessel rotation was initiated at 10 rotations per minute, and maintained for 10–16 days. Medium was changed every 2 to 3 days depending on glucose utilization. Concomitant with cells, microcarrier beads were added an 5 mg/ml to promote aggregate formation in the slow turning lateral vessel. Without beads the cells became shattered in the vessel in a few hours. Beads were cytodex-3 in all protocol except when electron microscopy was planned when the much more expensive, but easily sectioned Cultisphere GL cells were added to the vessels.

EXAMPLE 4

Stirred Controls and Static Controls

To provide a stirred control stirred fermentors which mixed in the horizontal plane were loaded with identical concentrations of cells and beads from the same pool added to the slow turning lateral vessel (1, 31, 46). Gas permeable Fluoroseal bags (Fluoroseal Inc, Urbana Ill.) in 7 or 55 ml size were selected as conventional static controls. Culture beads were added to the conventional controls at the same density as the slow turning lateral vessel cultures (1, 45).

EXAMPLE 5

Electron Microscopy Quantitation of Number of Microvilli

Transmission electron micrographs were performed on cell aggregates from the rotating wall vessels and conventional monolayers. Cells were washed with ice cold phosphate buffered saline, then fixed for electron microscopy with 2.5% glutaraldehyde in phosphate buffered saline (9, 47). The samples were then transferred to 1% osmium tetroxide in 0.05 M sodium phosphate (pH 7.2) for several hours, dehydrated in an acetone series followed by embedding in Epon. Lead-stained thin sections were examined and photographed using a Phillips EM/200 electron microscope. For electron microscopy the easily sectioned Cultispere GL beads, replaced Cytodex-3 which is almost impossible to section.

EXAMPLE 6

Analysis of the Proximal Tubule Epithelial Marker, g-glutamyl Transpeptidase

The renal cortical cells were 75+4% (n=4) proximal tubules as determined by flow cytometry analysis of aliquots for the proximal marker g-glutamyl transferase using Schiff base trapping of cleavage products of L-g-glu-4-methoxy-4-b-naphthylamine (44) (FIG. 1).

EXAMPLE 7

Analysis of the Endosomal Distribution of Megalin and Cubulin by Flow Cytometry

Figure 2A:
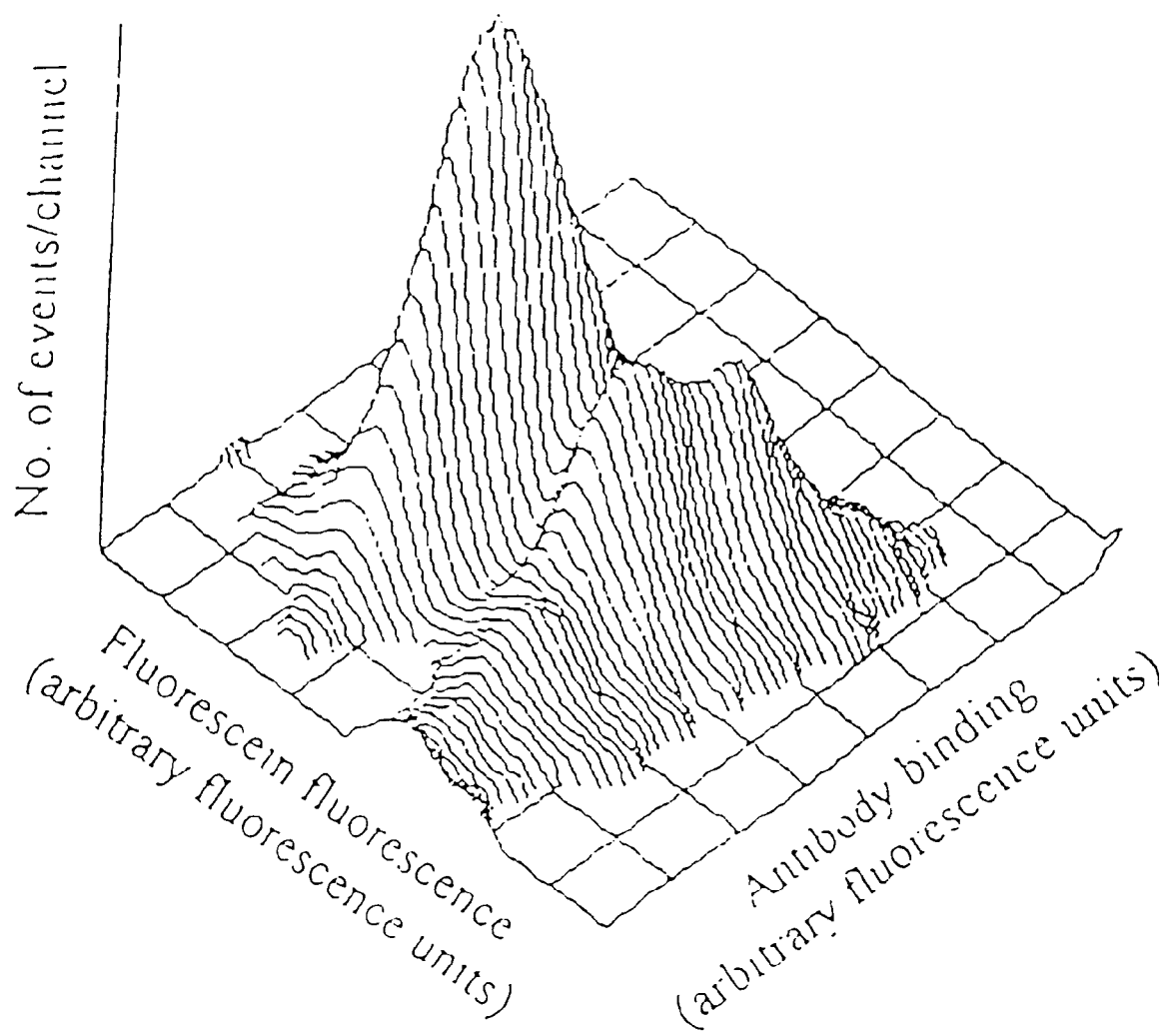
FIG. 2A shows analysis of the expression and endosomal compartmentation of megalin, and cubulin in renal cells following rotating wall vessel culture. The ability of flow cytometry to make simultaneous measurements of entrapped fluorescein dextran as an endosomal marker and antibody binding allows construction of three dimensional frequency histograms displaying entrapped fluorescein dextran fluorescence against antibody binding on horizontal axes. A control sample shows vesicles negative for fluorescein on the left and fluorescein containing endosomes on the right (2000 vesicles depicted left panel). A control without fluorescein entrapped shows only the left population (not shown). Co localization of anti-cubulin binding demonstrates that all the fluorescein positive endosomes are positive for cubulin, while non-endosomal membranes can be subdivided into cubulin positive and negative populations (middle panel). This pattern is repeated for anti-megalin binding in renal cortical cells (right panel).
Figure 2B:
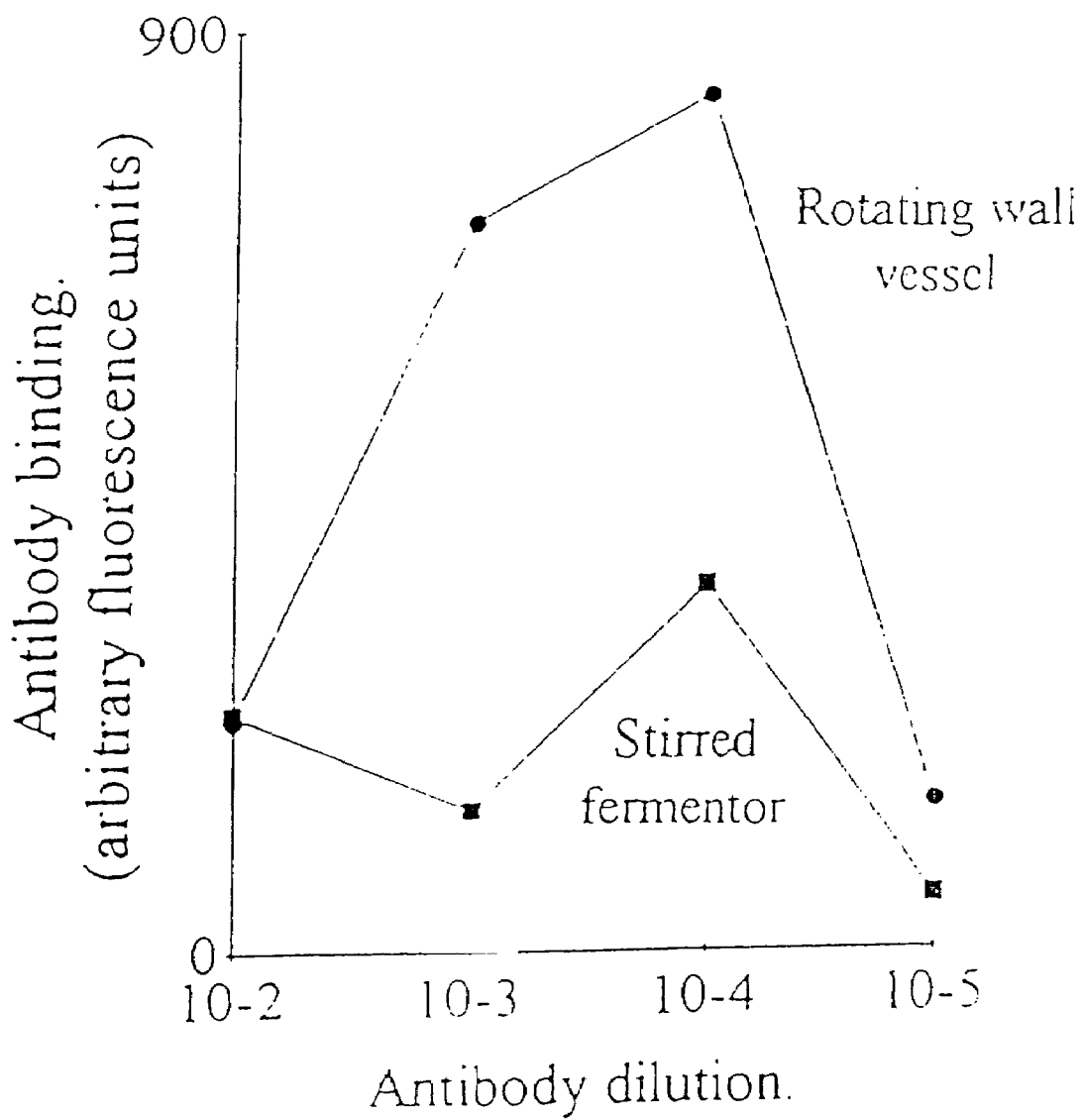
FIG. 2B shows quantitation of cubulin, and megalin antibody binding to renal cell membranes under various culture conditions. Analysis of protein expression in cultured cells by antibody binding used classic serial log dilution antibody curves. An increase in binding with a decrease in dilution is pathognomonic for specific antibody binding during flow cytometry analysis. Binding of anti-cubulin antisera to membrane vesicles prepared from renal cortical cells after 16 days in culture, detected by the fluorescence of a phycoerthyrein tagged secondary antibody, shows an almost two log increase in binding with antibody dilution (upper left panel below). This increased cubulin antibody binding in the cells grown in the rotating wall vessel (STLV) is more than five times the expression seen in stirred fermentors. Similarly, there was no detectable expression in the conventional cultures resulting in a flat line (not shown). Binding of normal serum and minimal dilution of primary antisera were not detectably different. Binding curves for anti-megalin antiserum showed a similar pattern (not shown).
Figure 2C:
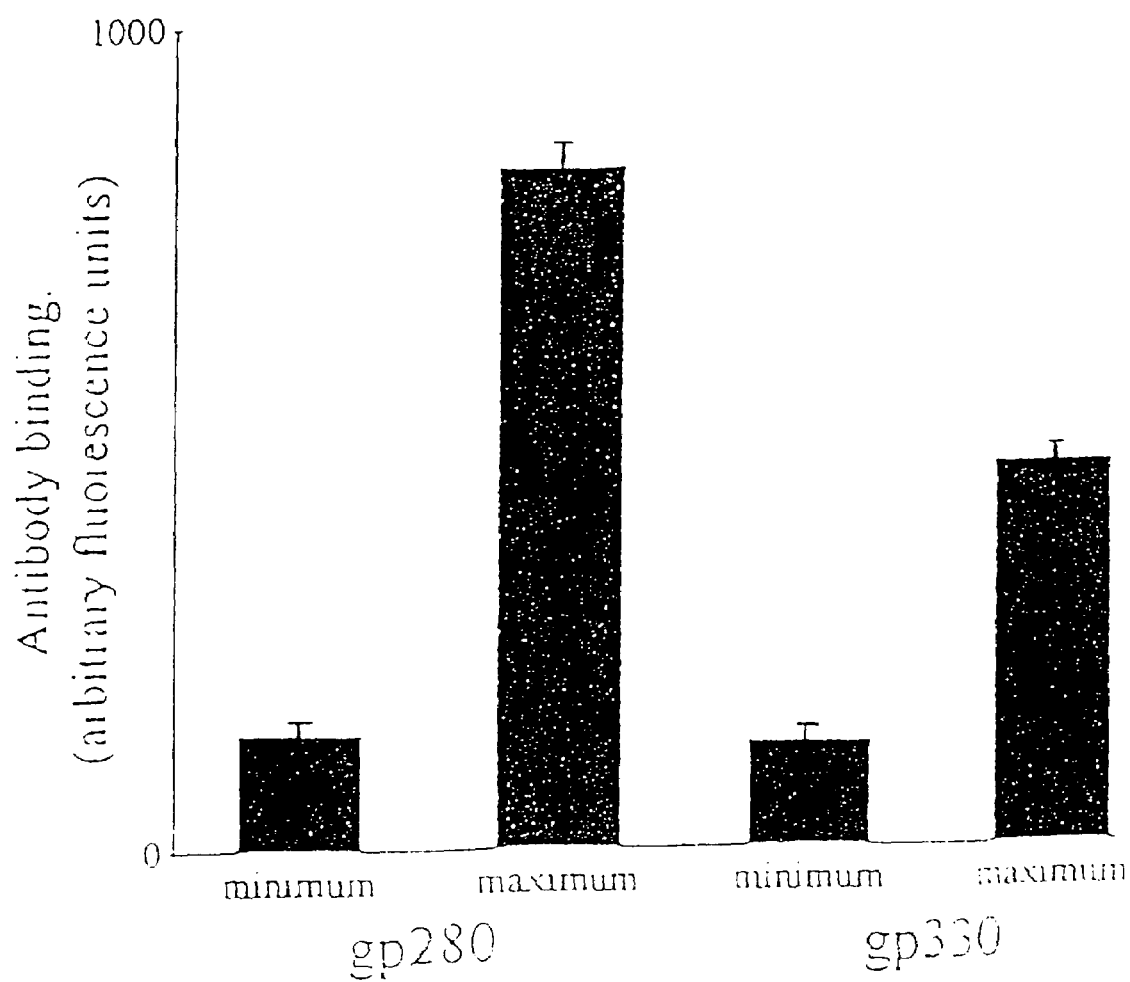
FIG. 2C depicts non-specific (minimum) and peak binding of each antiserum following rotating wall vessel culture and two-dimensional SDS-PAGE analysis of protein content of cells following rotating wall vessel culture. Analysis of the protein content of cultures of the natural mixture of rat renal cortical cells after 16 days culture in gas permeable bags as a control (left panel) or rotating wall vessel (right panel) depicts changes in a select set of proteins. Molecular weight (14–220 kDa) on the abscissa is displayed against isoelectric point (pH 3–10) on the ordinate.

To quantitate the total and endosomal expression of cubulin, megalin, and aquaporin-2 cells in conventional culture, stirred fermentors, and slow turning lateral vessels, 0.3 mg/ml 10S fluorescein-dextran was added to each cell culture for 10 minutes at 37° C. in the $CO_2$ incubator. This step loads an entrapped fluorescent dye into the early endosomal pathway (9, 47). Cells were then immediately diluted into ice cold phosphate buffered saline and washed once. Next, the cells were homogenized with 6 passes of a tight fitting glass-Teflon motor driven homogenizer. A post-nuclear supematant was formed as the 11,000 g supernatant, 180,000 g pellet of membrane vessels (FIGS. 2A–2C).

Aliquots of membrane vesicles were labeled with megalin or cubulin antisera. The megalin and cubulin antisera were rabbit polyclonals raised to affinity purified and chromatographically pure receptor (43, 48). Membrane vesicles were first pre-incubated in 50% normal goat serum for 2 hours to reduce non-specific binding of secondary antisera raised in goat. After washing aliquots of membrane vesicles were stained with serial log dilution of antisera and incubated at 4° C. overnight. After further washing 1:40 of goat anti-rabbit affinity purified rat pre-absorbed phycoerthyrein conjugated secondary antiserum was added, and incubated for 4 hours at room temperature. Prior to flow cytometry the membrane vesicles were washed and resuspended in 200 mM mannitol, 100 mM KCl, 10 mM HEPES, pH 8.0 with Tris to which had been added 10 mM nigericin. In the presence of potassium, nigericin collapses pH gradients, ensuring optimal fluorescence of the highly pH dependent fluorescein-dextran emission. Fluorescein-dextran and antibody staining tagged by phycoerythrein were now analyzed and co-localized on a vesicle-by-vesicle basis by flow cytometry (FIG. 2B).

EXAMPLE 8

Differential Display

Figure 3A:
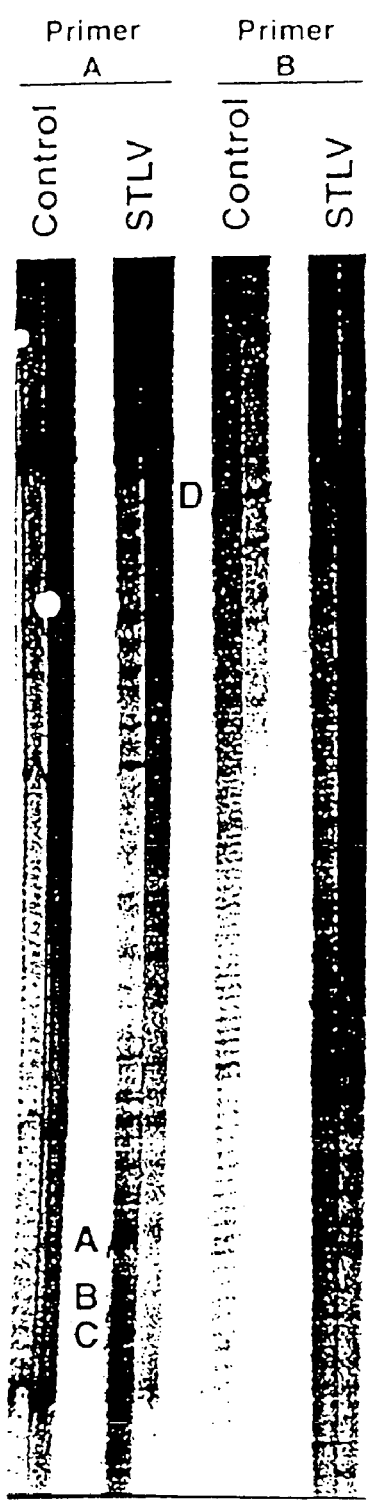

Differential display of expressed genes was compared in aliquots of the same cells grown in a 55 ml rotating wall vessel (slow turning lateral vessel) or conventional gas permeable 2-dimensional bag controls (FIGS. 3A and 3B). Differential display was performed using Delta RNA Fingerprinting system (Clontech labs, Palo Alto Calif.). Copies of expressed genes were generated by polymerase chain reaction using random 25 mer primers and separated on a 6% DNA sequencing gal. Bands of different intensity between control and slow turning lateral vessel, representing differentially expressed genes, were identified by visual inspection, excised and reamplified using the same primers. Differential expression and transcript size were confirmed by Northern hybridization. PCR products were then subcloned into the pGEM-T vector (Promega, Madison Wis.) and sequenced using fMOL cycle sequencing system (Promega, Madison, Wis.). Sequences were compared to the Genebank sequences using the BLAST search engine (National Center for Biotechnology Information). For genes of interest the bands were labeled with 32P for confirmation of the changes by Northern blot analysis.

EXAMPLE 9

Detection of Gene Expression in Cell Cultures by RT-PCR

Figure 3C:
FIG. 3C and FIG. 3D show RT-PCR of time dependent change in genes during rotating wall vessel culture. Semi quantitative RT-PCR shows increases in the epithelial genes megalin, villin and extra-cellular calcium sensing receptor (ECaR), the shear stress response element genes ICAM, VCAM and MnSOD (FIG. 3C). There was no change in b-actin or GADPH. Unlike in endothelial cells many of these changes are prolonged as at 16 days megalin, ECaR, ICAM, VCAM and villin changes persist (FIG. 3D).
Figure 3D:
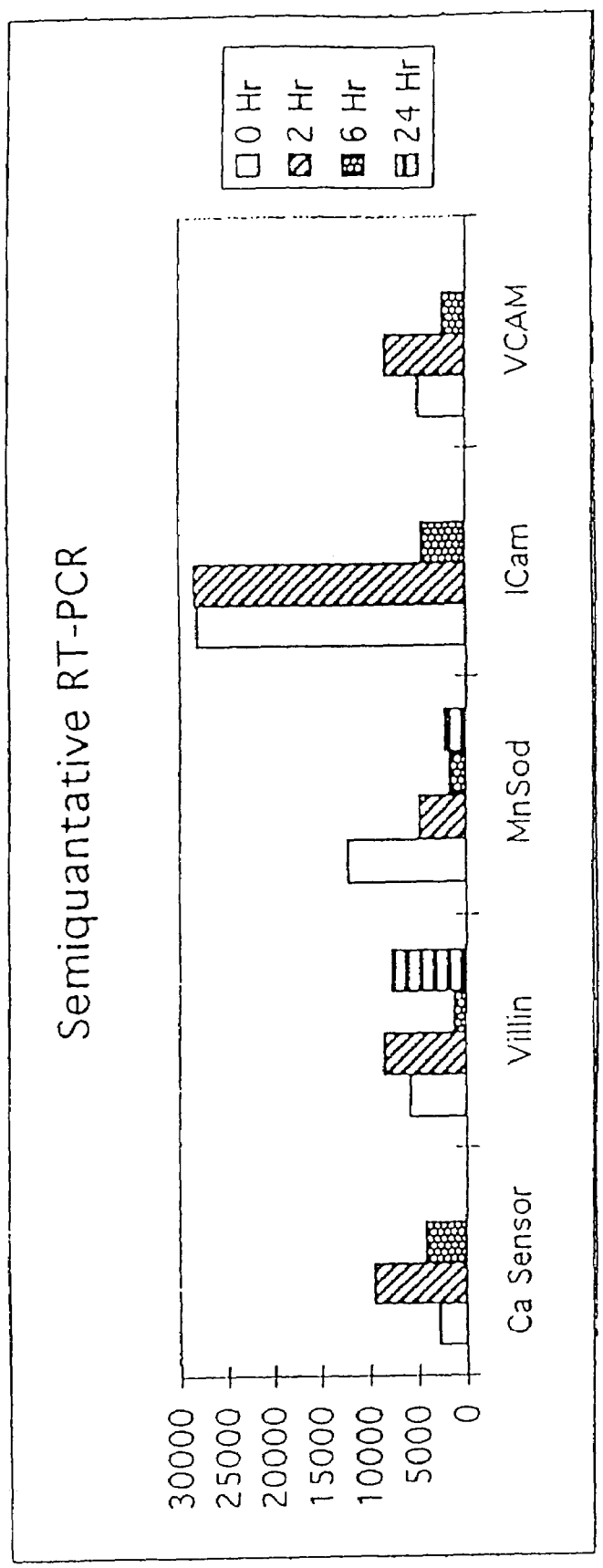

Cell aggregates from the rotating wall vessel culture were washed once in ice cold phosphate buffered saline and snap frozen at −70° C. until RNA was isolated. Total RNA was first isolated, followed by isolation of poly A+ RNA. Following reverse transcription, 10%–20% of each cDNA was amplified (Robocycler 40, Stratagene, La Jolla, Calif.) using 95° C. denaturation, 63° C. annealing and 72° C. extension temperatures. Amplification was for a total of 30 cycles with the first three cycles having extended denaturation and annealing times. Positive and negative strand PCR primers, respectively, were derived from published sequences using Genetunner software. 20% of the PCR reaction was electrophoresed on agarose/ethidium bromide gels and visualized under UV light so that a comparison of amplified gene fragments could be made to DNA standards (HaeIII digested X174 DNA, Promega) electrophoresed on the same gel (FIGS. 3C and 3D). Representative fragments amplified for each gene in question were isolated from gels and direct sequenced to assure identity of the PCR product. In addition, 5% of the same cDNA were subjected to PCR for expression of the housekeeping mRNA, glyceraldehyde 3-phosphate dehydrogenase, and b-actin to assure that similar amounts of input RNA and that similar efficiencies of reverse transcription were being compared. Each cDNA was run in at least three dilutions to ensure that measurements were made on the initial linear portion of the response curve.

EXAMPLE 10

Genetic Decoys

Double stranded genetic decoys matching the sequence of a known shear stress response element were synthesized (Chemicon International Inc., La Jolla, Calif.) (structure and sequence shown in FIG. 4A). These decoys had a terminal phosphothioate moiety to prevent intracellular lysis, and a phosphodiester backbone to facilitate passage across cell membranes (49). Passage to and accumulation in the nuclear compartment of cultured cells was confirmed by confocal imaging of a fluorescein tagged decoy. Three decoys were synthesized: the active decoy, a random sequence control in which the six bases of the shear stress response element were scrambled, and a fluorescein conjugated form of the decoy. Decoys were placed in the cell culture medium of rat renal cortical cells grown as above in conventional two-dimensional culture. Aliquots of cells exposed to control or active sequence decoy at 80 nm concentration were harvested at 2, 6, and 24 hours after exposure.

EXAMPLE 11

Genetic Discovery Array

A sample of human renal cortical cells grown in conventional flask culture was trypsinized and split into a gas permeable bag control and a rotating wall vessel (55 ml slow turning lateral vessel). After 8 days of culture on 5 mg/ml cytodex-3 beads, cells were washed once with ice cold phosphate buffered saline, the cells were then lysed and mRNA was selected with biotinylated oligo(dT) then separated with streptavidin paramagnetic particles (PolyATtract System 1000, Promega Madison, Wis.). 32P labeled cDNA probes were then generated by reverse transcription with 32P dCTP. The cDNA probes were hybridized to identical Gene Discovery Array Filters (Genome Systems Inc. St. Louis, Mo.). The Gene Discovery Array filters contain 18,394 unique human genes from the I.M.A.G.E. Consortium [LLNL](15) cDNA Libraries which are robotically arrayed on each of a pair of filter membranes. Gene expression was then detected by phosphor imaging and analyzed using the Gene Discovery Software [Genome Systems] (50).

EXAMPLE 12

Assay of 1-a-hydroxylase Activity

As the 1-a-hydroxylase enzyme has never been isolated or cloned it is assayed functionally by the production of 1,25-dihydroxy-vitamin D3 from ultrapure exogenous 25-hydroxy vitamin D3. For each measurement, the classic. Michaelis Menton kinetics of the enzyme are determined by assaying equal aliquots of renal cell aggregates in a curve of 25-OH D3 substrate concentrations from 0.1 to 10 mg/ml in 6 steps. All incubations are performed in the presence of the anti-oxidant DPED at 10 mM to ensure no contribution of non-enzymatic oxygenation (23–26). 1,25-diOH D3 generated in vitroβwas quantitated as described (23–27). In vitroβincubations were terminated by adding a volume of acetonitrile equal to the incubation volume. Each incubation tube received 1,000 cpm of 3H-1,25 dihydroxy D3 to estimate recovery losses during the extensive extraction and purification scheme. The 1,25-dihydroxy D3 is extracted from the incubation medium by C18 solid-phase extraction (24–25). Following extraction, the samples are evaporated to dryness under N2 and dissolved in 2 ml of methylene chloride. The samples are then applied to silica Bond-Elut cartridges and the 1,25-dihydroxy D3-containing fraction is isolated and collected (26). The individual fractions containing 1,25-diOH D3 and then subjected to normal phase HPLC on a Beckman model 344 liquid chromatography system. Normal-phase HPLC was performed with a Zorbax-Sil column (26) (4×25 cm) developed in and eluted with methylene chloride/isopropanol (96:4 v/v) with a flow rate of 2 ml/min. The 1,25-dihydroxy D3 eluted from this system was dried under N2 resuspended in ethanol and quantitated by radio receptor assay or radio immunoassay (25–26). Plasma 1-25-dihydroxy vitamin D3 was assayed in a similar fashion, but as the product is already formed, assay begins with extraction into acetonitrile (23–26). Hence, all measurement of 1-a-hydroxylase activity in cells included determination of the Michaelis Menton Km and Vmax, of the enzyme. The Michaelis Menton parameters were determined by automated curve fitting.

EXAMPLE 13

Culturing Renal Fibroblasts and Assay for Production of Erythropoietin

As renal fibroblasts are the source of erythropoietin secreted into the circulation, renal fibroblasts were cultured. Freshly dissected rat renal cortex was minced and collagenase\trypsin digested prior to removal of debris on a single discontinuous 5% albumin gradient. The mixture of rat renal cortical cells was placed into culture in DMEM\F12 with 20% fetal bovine serum. After two weeks to encourage fibroblast overgrowth in the rich medium, fibroblast growth factor was added. The resultant culture had fibroblastic features in the culture flask and was inoculated into a high aspect rotating vessell (HARV) for culture under increased shear stress conditions. The cells aggregate on the beads and slowly increasing their numbers. After 3 weeks growing the fibroblasts in a HARV, erythropoietin was assayed in the cell supernatant. The media were concentrated 15× and assayed via RIA. The media alone was also concentrated 15× as the control.

EXAMPLE 14

Culturing Hepatocytes and Assay for Production of Erythropoietin

As hepatocytes are a source of erythropoietin secreted into the circulation, immortalized human hepatocytes were cultured under control and subjected to shear stress conditions. The Hep3B cells were placed into culture in DMEM with 10% fetal bovine serum in a static flask culture. The resultant culture was split, one half remaining in static flask culture and the other half inoculated into a HARV for culture under increased shear stress conditions. The cells aggregated on the beads. After 24 hours of growing the Hep3B cells in a HARV, erythropoietin was assayed in the cell supernatant. The media were assayed by RIA. The static flask media was also assayed as the control.

EXAMPLE 15

Shear Stress Response Elements Mediate Changes in Erythropoietin Gene Expression The immortal hepatic cell line, Hep3B, constitutively produces erythropoietin. The 5' promoter and 3' enhancer regions of the gene contain putative shear stress response elements. The role of these elements in the enhancement of erythropoietin production in response to shear was tested by using integrated perfused rotating wall vessel culture to reintroduce graded shear. This protocol utilizes a library of promoters driving luciferase reporters genes, with various constructs lacking the putative shear stress response elements. It also allows DNTA footprinting analysis of the histones which bind the promoter and enhancer elements.

EXAMPLE 16

Results

The proportion of proximal tubular cells in human renal cell fractions isolated by differential trypsinization was assayed using an entrapped fluogenic substrate for the proximal enzyme marker g-glutamyl-transferase (44). Flow cytometry analysis on a cell-by-cell basis showed the natural cell mixture in the human renal cortex to be 85+4%, n=4 proximal tubular cells (FIG. 1A, left panel). Following differential trypsinization, and selection of the pure fractions, proximal tubular enrichments as high as 99+1% could be achieved (right panel). As reported in other systems, rotating wall vessels were conducive to vigorous cell growth, as evidenced by the high rates of glucose consumption assayed as 30 mg/dl glucose/100,000 cells/day. A cell doubling time of 4+3 days was assayed using Alamar blue in the rotating wall vessel compared to 4+2 days in conventional culture (n=4).

Figure 1B:
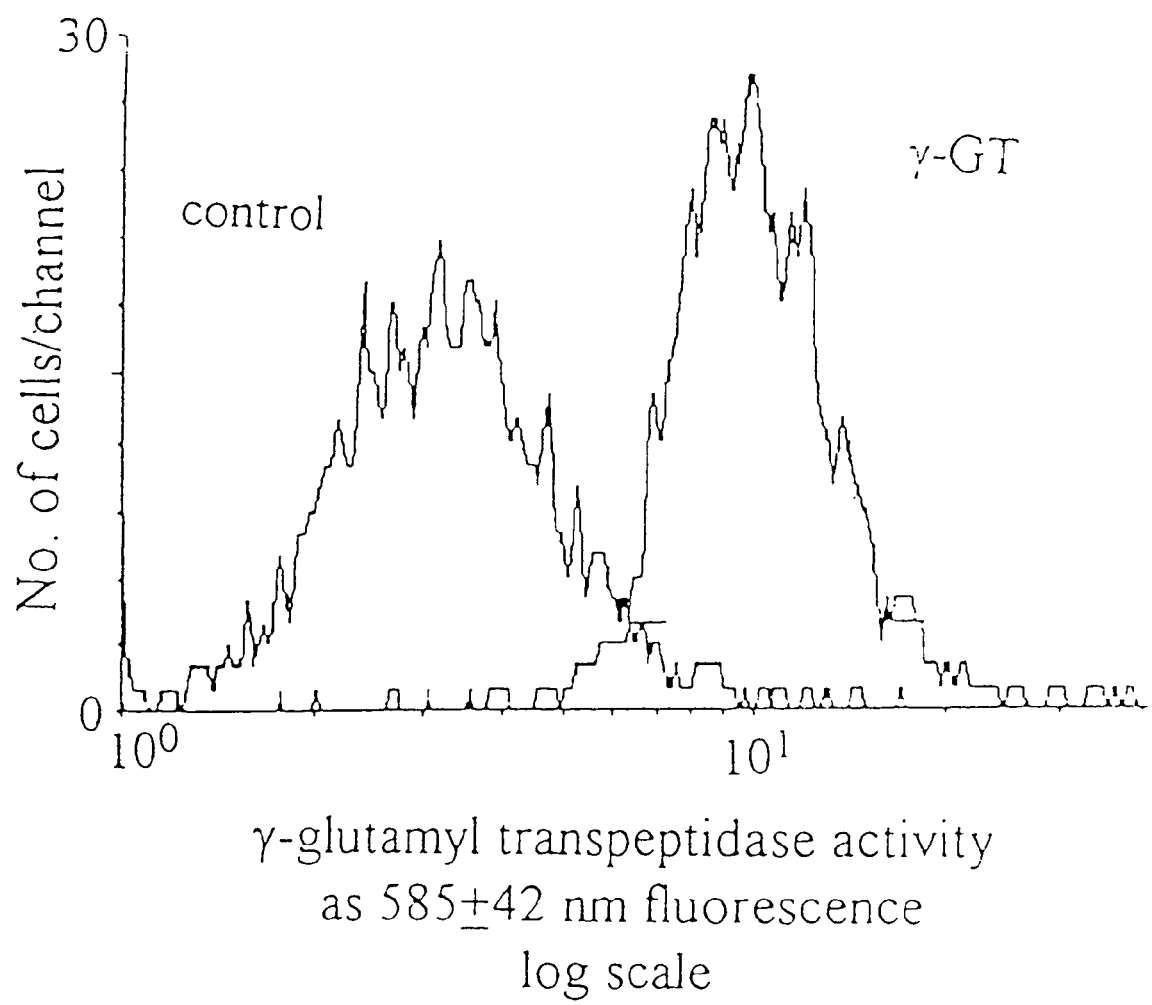
FIG. 1B shows that following differential trypsinization, the percentage of proximal tubular cells present can be increased to 99±1%.
Figure 1C:
FIGS. 1C and 1D show transmission electron micrographs of human epithelial cells in culture. The intact renal cortex in vivo (far left panel), is compared to culture of the natural mixture of human renal cortical cells in conventional 2-dimensional culture (middle left panel) which is completely devoid of microvilli. Rotating wall vessel culture of pure proximal tubular cells shows some microvilli (middle right panel) but there are far more microvilli during rotating wall vessel culture of the natural mix of renal cortical cells (far right panel). Compared to these representative images, some areas of the natural mixture of cells in the rotating wall vessel show much greater abundance of microvilli, and well defined desmosomes (lower panel) which are lacking in the other cultures.
Figure 1D:

The ultrastructure of cultures of pure proximal tubular cells or renal cortical cell mixtures of human kidneys were grown in rotating wall vessels for 16 days, and were examined by transmission electron microscopy (FIGS. 1B and 1C). Quantitation of the number of microvilli present by counting random plates at the same magnification demonstrates not only that the rotating wall vessel induces microvillus formation, but co-culture with the normal mix of renal cortical cells increases the effect (Table 1). Normal cortical cell mix in conventional two-dimensional culture has 21 microvilli per field; "pure" proximal tubular culture in rotating wall vessel has 104 microvilli per field; and the normal cortical cell mix in rotating wall vessel has 3511 microvilli per field.

TABLE 1

Human proximal tubular cells microvilli counted on transmission electronmicrographs of cells grown for 16 days under various culture conditions

| Culture Conditions | % Proximal Tubular Markers | Microvilli Per Field |
| --- | --- | --- |
| conventional 2-D culture | 85 | 2 1 |
| pure+ culture in rotating wall vessel | 99 | 10 4 |
| normal cortical cell mix in rotating wall vessel | 85 | 35 11 |

To examine the expression of megalin and cubulin in renal cells in culture, there are advantages to using human cells instead of rat cells. Specifically, the rat sequences of megalin and cubulin have been cloned, while the human sequences have not, and the antisera recognizes the rat but not the human isoforms of these proteins. Hence, the natural mixture of cells in the rat renal cortex was placed into culture in rotating wall vessels, stirred fermentors, and traditional culture for analysis of protein expression.

As the endosomal pathway has been implicated to play a central role in the function and pathophysiology of cubulin and megalin, entrapped endosomal markers were co-localized with receptor antibody binding. The ability of flow cytometry to make simultaneous measurements of entrapped fluorescein dextran as an endosomal marker and antibody binding allows construction of three dimensional frequency histograms displaying entrapped fluorescein dextran fluorescence against antibody binding on horizontal axes and number of vesicles in each channel up out of the page (FIG. 2A). A control sample shows vesicles negative for fluorescein on the left and fluorescein containing endosomes on the right (200 vesicles depicted, left panel). A control without fluorescein entrapped shows only the left population (not shown). Co localization of anti-cubulin binding demonstrates that all the fluorescein positive endosomes were positive for cubulin, while non-endosomal membranes could be subdivided into cubulin positive and negative populations. (middle panel). This pattern was repeated for anti-megalin binding in renal cortical cells (right panel) in culture.

Next, analysis of protein expression in cultured cells by antibody binding used classic serial log dilution antibody curves. An increase in binding with a decrease in dilution is pathognomonic for specific antibody binding during flow cytometry analysis. Binding of anti-cubulin antisera to membrane vesicles prepared from renal cortical cells after 16 days in culture, detected by the fluorescence of a phycoerthyrein tagged secondary antibody, shows an almost two log increase in binding with antibody dilution (FIG. 2B). This increase in the cells grown in the rotating wall vessel (slow turning lateral vessel) is more than five times the expression seen in stirred fermentors. Similarly there was no detectable expression in the conventional cultures resulting in a flat line (not shown). Comparison of maximal binding of the anti-cubulin antibody to minimum taken to be the antibody dilution at which there is no further decline in signal with primary antibody dilution is shown in FIG. 2C. Binding of normal serum and minimal dilution of primary antisera were not detectably different. Binding curves for anti-megalin antiserum showed a similar pattern (not shown) but the peak binding was a little lower (FIG. 2C). Again stirred fermentor has much less expression than the rotating wall vessel (slow turning lateral vessel) and the conventional cell membranes have no detectable binding (not shown).

To examine the proportion of proteins changing in the rotating wall vessel, two-dimensional gel SDS-PAGE analysis on cultures grown in the rotating wall vessel and bag controls were performed (FIG. 2d). The results shown in FIG. 2D demonstrates changes were in a selected group of proteins.

To identify the genes changing during rotating wall vessel culture, differential display were performed. Differential display of expressed genes was compared in aliquots of the same cells grown in a 55 ml rotating wall vessel (slow turning lateral vessel) or conventional gas permeable 2-dimensional bag controls. Differential display of copies of expressed genes were generated by polymerase chain reaction using random 25 mer primers and separated on a 6% DNA sequencing gel. Bands of different intensity between control and slow turning lateral vessel, representing differentially expressed genes, were identified by visual inspection, excised and reamplified using the same primers. Differential expression and transcript size were confirmed by Northern hybridization. PCR products were then subcloned into the pGEM-T vector and sequenced. Sequences were compared to the Genebank sequences using the BLAST search engine. One expressed gene which decreased in the slow turning lateral vessel (band D on gel, FIG. 3A) was identified as rat manganese-containing superoxide dismutase (98% match 142 of 144 nucleotides). Two genes which increased in the slow turning lateral vessel, band A was identified as the interleukin-1 beta gene (100% match for 32 of 32 nucleotides) and Band B which corresponded to a 20 kB transcript on a Northern blot appears to be a unidentified gene that has a 76% homology to the mouse GABA transporter gene.

To examine the genetic changes in specific genes, the expression of tissue specific epithelial cell markers and classic shear stress response dependent genes were examined by RT-PCR (FIG. 3c). Several genes specific for renal proximal tubular epithelial cells, including megalin, cubulin, the extracellular calcium sensing receptor, and the microvillar structural protein villin, increase early in rotating wall vessel culture. Similarly there were dynamic time dependent changes in classic shear stress dependent genes including intercellular adhesion molecule 1 (ICAM) and vascular cell adhesion molecule (VCAM) (increased) and manganese dependent superoxide dismutase (suppressed). Many but not all of these changes were prolonged, as after 16 days in culture gene expression of megalin, ICAM, VCAM and the extracellular calcium sensing receptor were still elevated, while villin and manganese dependent superoxide dismutase were at control levels. Expression of control GADPH, b-actin and 18S genes did not change throughout the time course.

Figure 4A:
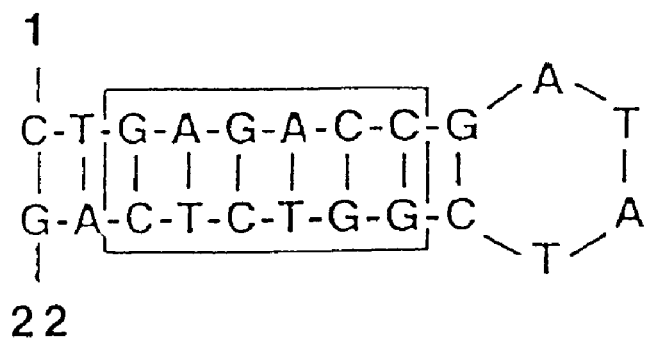
FIG. 4A shows the structure. The probe with sequence CTGAGACCGATATCGGTCTCAG (SEQ ID No:1) has two possible conformations. As a single strand it would fold back on itself to form a binding element for the transcription factor. As a double strand it would then have two binding sites for the transcription factor, one in the sense orientation and one in the antisense orientation.
Figure 4A:
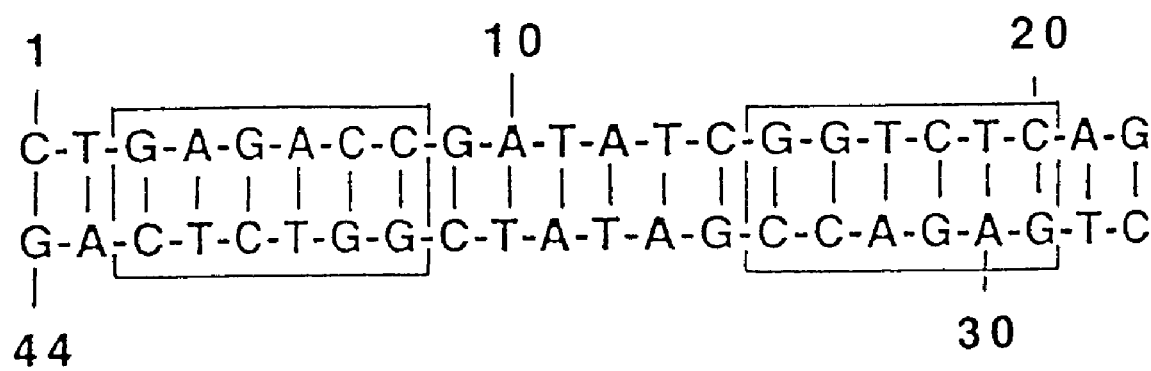
Figure 4B:
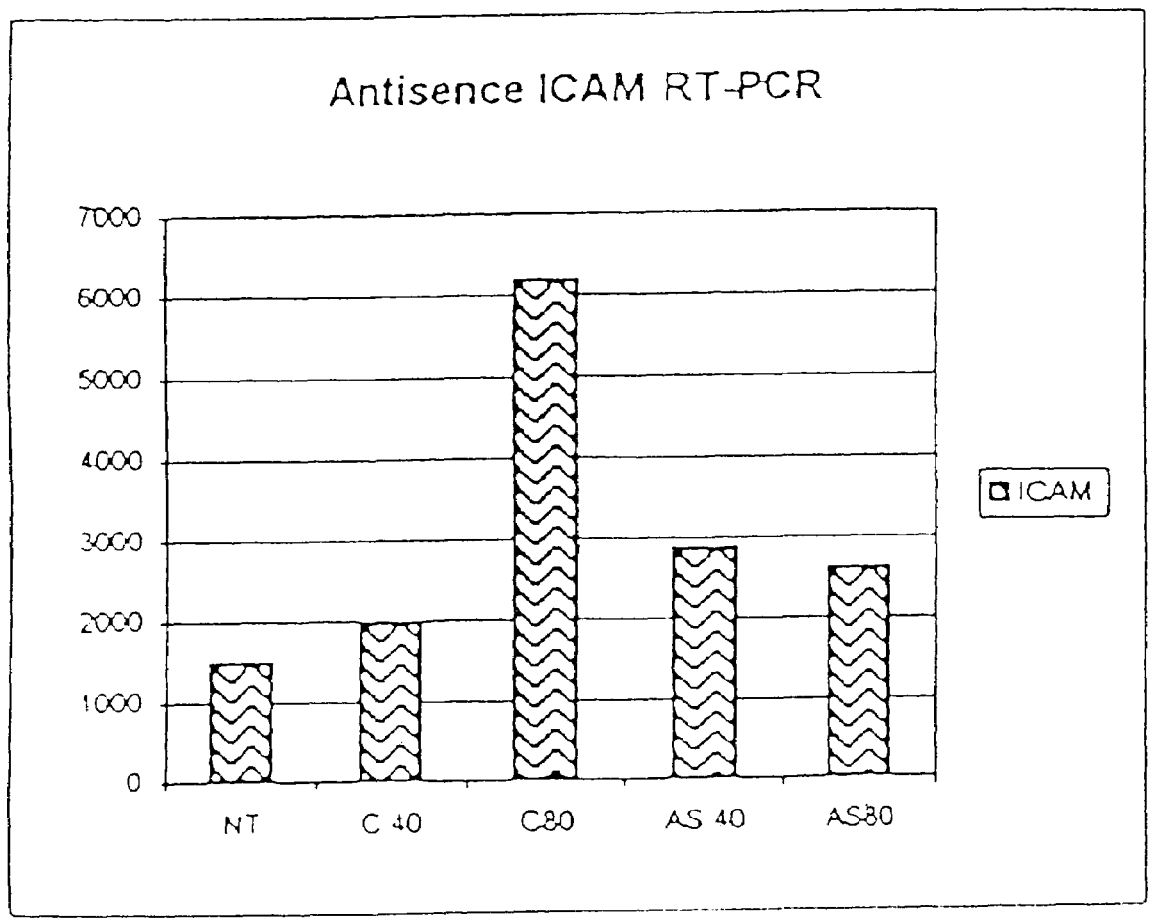
FIG. 4B shows effects of antisense shear stress response element probe on time dependent gene expression. The antisense probe added to conventional 2-dimensional cultures of rat renal cortical cells at 80 nm increases MnSOD in a time dependent manner. Comparison is made to controls with the active binding site scrambled. In contrast the probe has no effect on villin gene expression.
Figure 4B:
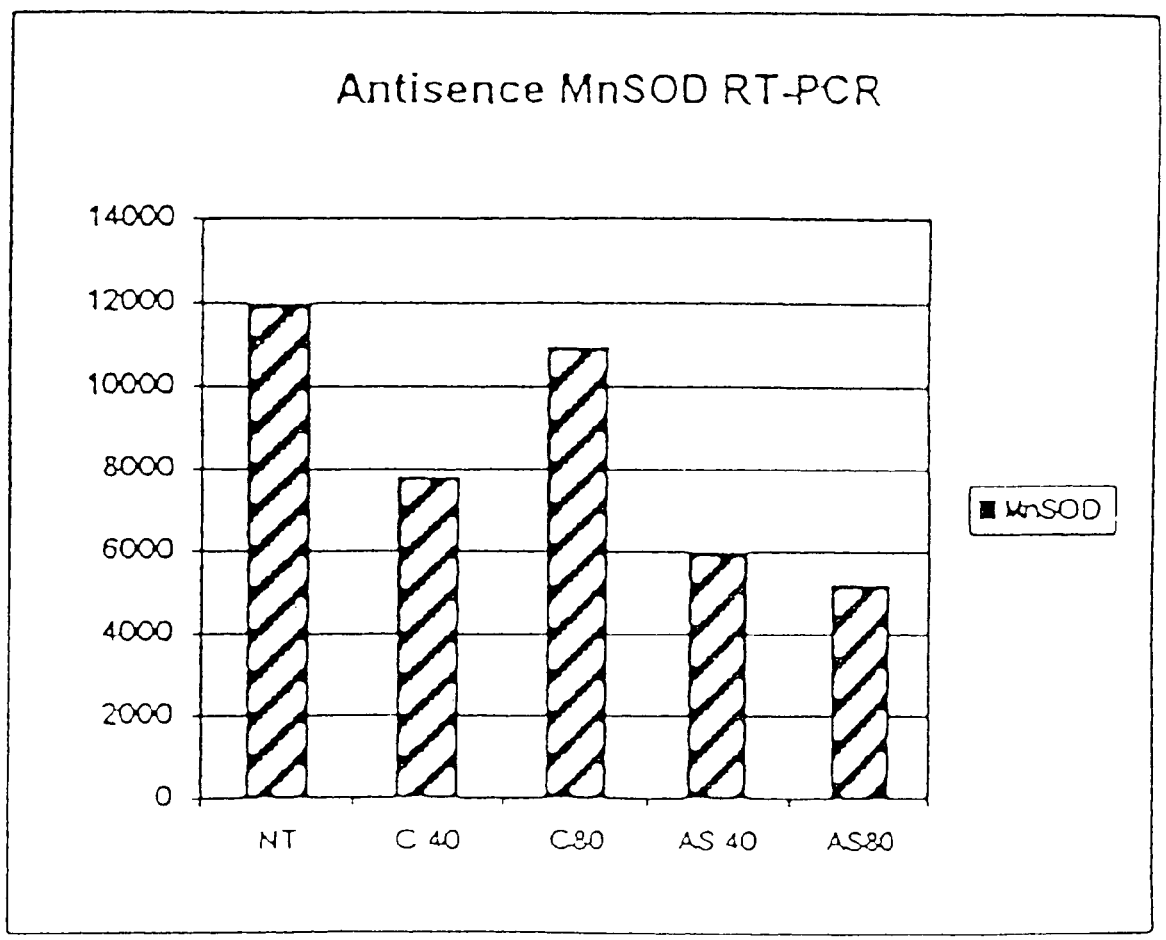

To test for a role of a putative endothelial shear stress response element in these renal cortical cell changes, an antisense probe for the sequence was synthesized (FIG. 4A). A control probe had the active motif scrambled. Confocal imaging of a fluorescein conjugated form of the probe confirmed nuclear delivery of the probe (images not shown). Culture of rat renal cortical cells in 80 nm of the probe, resulted in a time dependent increase in magnesium dependent superoxide dismutase, but no change in villin gene expression (FIGS. 4B and 4C). The control probe had no effect.

Figure 5:
FIG. 5 shows gene expression in the rotating wall vessel: automated gene analysis. Abundance of the expression of over 18,300 genes was assayed by annealing poly A RNA from human renal cortical epithelial cells grown in a rotating wall vessel for 8 days to a filter robotically loaded with oligonucleotide primers. Poly A RNA from a non adherent bag culture serves as a control. The filters are shown at the top of the diagram then the analysis of shear stress responsive genes, renal epithelium specific genes, and other genes germane to the current analysis.
Figure 5:
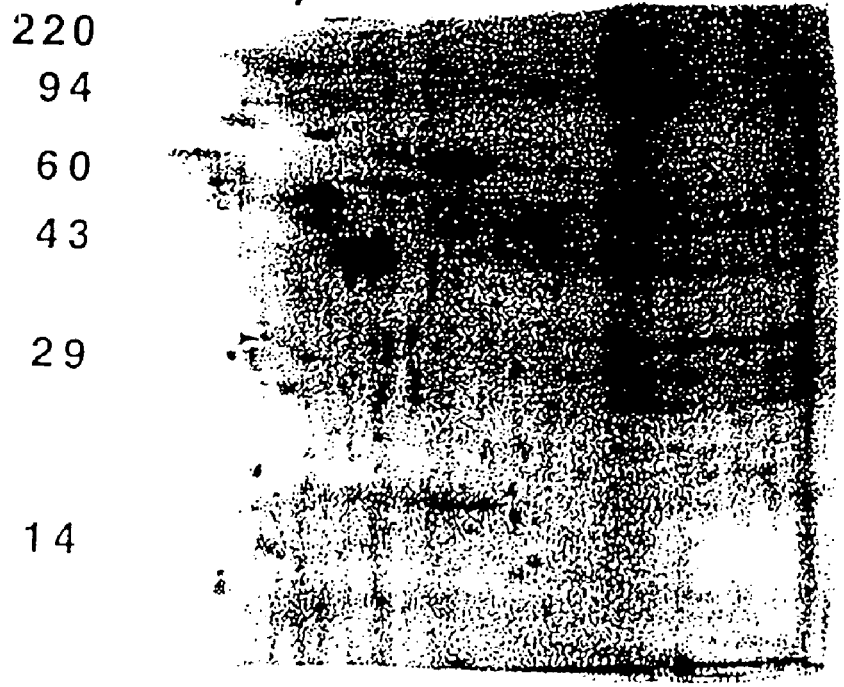

In order to confirm the genetic responses to rotating wall vessel culture and the analysis with human cells, automated gene display analysis of expressed RNA was performed on human renal cortical cells grown in a control gas-permeable bag and the slow turning lateral vessel for 8 days (50). Of the more than 18,000 genes assayed a select group was again observed to change (FIG. 5). In particular, vectored changes in all the classic shear stress response genes assayed by RT-PCR and differential display in rat cell culture were confirmed. A battery of tissue specific genes was increased including villin, angiotensin converting enzyme, parathyroid hormone receptor and sodium channels. Other physical force dependent genes such as heat shock proteins 27/28 kDa and 70-2 changed, as did focal adhesion kinase, and a putative transcription factor for shear stress responses NF-kb changed. Fusion proteins such as synabtobrevin 2 mildly decreased gene expression, and clathrin light chains hugely increased gene expression.

To determine whether renal cells grown in simulated microgravity have 1-a-hydroxylase activity, the 1-a-hydroxylase activity of cell cultures were compared grown in traditional 2-D culture in gas permeable bags, and NASA rotating wall vessels. Both rat renal cells (Table 2) and human embryonic renal cells were assayed (Table 3).

TABLE 2

The 1 a-hydroxylase activity of the various rat renal cell cultures detected as production of 1,25-diOH D3

| Cell Sample | 1,25-diOH D3 concentration (pg/ml) | Volume of Supernatant (ml) | 1,25-diOH D3 Production (pg) |
|---|---|---|---|
| Boiled static control I | <2, not detectable | 7 ml | Not detectable |
| Boiled static control II | <2, not detectable | 7 ml | Not detectable |
| Static control I | <2, not detectable | 7 ml | Not detectable |
| Static control II | <2, not detectable | 7 ml | Not detectable |
| Boiled rotating wall vessel | <2, not detectable | 55 ml | Not detectable |
| Rotating wall vessel | 14.2 | 55 ml | 781 |

The results shown in TABLE 2 indicate that rat renal cells show increased structural differentiation during culture in simulated microgravity conditions, and express much greater 1-a-hydroxylase activity than under conventional culture conditions.

TABLE 3

The 1 a-hydroxylase activity of the various human embryonic renal cell cultures detected as production of 1,25-diOH D3

| Cell Sample | 1,25-diOH D3 Concentration (pg/ml) | Volume of Supernatant (ml) | 1,25-diOH D3 Production (pg) |
|---|---|---|---|
| Boiled static control | 8.2 | 10 | 82 |
| Static control | 14.6 | 10 | 146 |
| Rotating wall vessel | 24.8 | 55 | 1364 |

TABLE 3 indicates that human embryonic kidney cells show increased structural differentiation during culture in simulated microgravity conditions, and express 10 foid greater 1-a-hydroxylase activity than under conventional culture conditions.

TABLE 4

Renal fibroblasts cell supernatant erythropoietin assay

| Condition | Erythropoietin (mu/ml) |
|---|---|
| Shear stress culture | 1.8 |
| Control media conc 15X | 0.23 |

TABLE 5

Hepatocytes cell supernatant erythropoietin assay

| Condition | Erythropoietin (mu/ml) |
|---|---|
| Shear stress culture | 141.7 mu/1 × 106 cells |
| Control static flask | undetectable |

Results of cell supernatant erythropoietin assay from renal fibroblasts and hepatocytes culture were shown in Table 4 and Table 5, respectively. The results shown in TABLES 4 and 5 indicate erythropoietin production was increased in both renal and hepatic cells during graded gravitational sedimentation shear.

Erythropoietin has the classic shear stress response elements in the promoter and enhancer regions which control expression of its gene. The results shown in Tables 4 and 5 also indicate that the expression of the erythropoietin gene was upregulated by those shear stress response elements during graded gravitational sedimentation shear in the vessel.

EXAMPLE 17

Discussion

Rotating wall vessels have been used by other investigators as "simulated microgravity". The present invention contends that gravity is still active, and that in a rotating wall vessel gravity is balanced by equal and opposite sedimentational shear stress. A centrifugal force due to spinning the cells, quantitatively much smaller than gravity, is also present and offset by equal and opposite sedimentational shear stress. Thus, the present invention presents a new concept that rotating wall vessels provide this new balance of forces, including application of sedimentational shear, rather than microgravity.

The rotating wall vessel bioreactor provides quiescent co-localization of dissimilar cell types (1, 46), mass transfer rates that accommodate molecular scaffolding and a microenvironment that includes growth factors (1, 46). Engineering analysis of the forces active in the vessel is complex (1, 5–7). This study provides the first evidence for the cell biological mechanisms by which the vessel induces changes in tissue specific gene and protein expression.

There are two possible explanations why the rotating wall vessel induces an order of magnitude more expression of the renal toxin receptors cubulin and megalin than stirred fermentor culture. First, there are significant differences in the degree of shear stress induced. The rotating wall vessel induces 0.5–1.0 dynes/cm2 shear stress (1), while stirred fennentors induce 2–40 dynes/cm2 depending on design and rotation speed (1, 5, 46). This degree of stress damages or kills most epithelial cells (1, 5, 46). Second, impeller trauma in the stirred fermentor, is absent in the rotating wall vessel. This explains why there was far more cubulin and megalin induced in renal cultures in rotating wall vessel culture than a stirred fermentor, and both receptors were not detectable in conventional 2-dimensional culture.

Rotating wall vessel culture induced changes in a select set of genes, as evidenced by the genetic differential display gels and 2-dimensional protein gel analysis. For example, erythropoietin production is controlled by a shear stress element which mediates changes observed during graded gravitation sedimentation shear. 1-a-hydroxylase activity is maintained and increased in both renal cortical epithelial cells and human embryonic kidney cells, wherein the induction of the enzyme (1-a-hydroxylase) converts 25-hydroxy-vitamin D3 to the active 1,25-dihydroxy-vitamin D3 form. The present invention is the first demonstration of a process for production of molecules including hormones and other biomolecules induced by shear stress and other forces. The mechanistic information can be interpreted from knowledge of the pattern of response and distribution of certain gene products.

Megalin and cubulin represent the first pattern of change, as these proteins are restricted in distribution to renal cortical tubular epithelial cells. The increase in megalin mRNA and protein, and cubulin protein expression is therefore unequivocal evidence for changes in the epithelial cells. This provides an important new tool for studies of nephrotoxicity. Long suspected to play a role in renal toxicity, the tissue restricted giant glycoprotein receptors megalin and cubulin, have recently been shown to be receptors for common nephrotoxins. Megalin is a receptor for polybasic drugs such as the aminoglycoside antibiotic gentamicin (48) and vitamin D binding protein (51), and cubulin is the receptor for vitamin-B12 intrinsic factor (52). Although these receptors are expressed by transformed placental cells in culture (9, 43), there is currently no renal model expressing these markers for toxicology investigations (53). Rotating wall culture provides a fresh approach to expression of renal specific markers in culture for study on the pharmacology, biochemistry and toxicology which define the unique properties and sensitivities of renal epithelial cells.

The second pattern of change is represented by villin. Message for the microvilli protein villin increases in the rotating wall vessel in the first day of culture, and soon reformation of microvilli was observed. A decoy matching the nuclear binding motif of a putative shear stress response element failed to induce similar changes. Although the promoter for villin has not been cloned, this suggests the changes in villin were induced by other transcription factors which may be due to shear stress or other stimuli in the bioreactor. Villin is also restricted to brush border membranes such as renal proximal tubular cells, or colonic villi (54–55). The observed increases in villin message resolved after 16 days of rotating wall vessel culture.

Magnesium dependent superoxide dismutase represents a third pattern of response: a mitochondrial enzyme, ubiquitous is distribution, modulated by the classic shear stress response element in endothelial cells (56–57). Magnesium dependent superoxide dismutase message decreased early in the first day of rotating wall vessel culture, and this was persistent after 16 days in culture. These changes were confirmed when magnesium dependent superoxide dismutase was identified as suppressed in the differential display analysis of gene changes, and Northern blot confirmation was performed. A decoy for the classic shear stress response element induced an increase in magnesium dependent superoxide dismutase (MnSOD), which indicates that similar changes to the rotating wall vessel can be induced by the use of genetic decoys. Thus, the biological process of genetic induction by defined shear stress elements can be produced by multiple means including genetic decoys or use of the rotating wall vessel. Other shear stress response element dependent genes, specifically, intercellular adhesion molecule 1 (ICAM) and vascular cell adhesion molecule (VCAM) had changes in the rotating wall vessel opposite to magnesium dependent superoxide dismutase, mirroring observations made during flow induced stress in endothelial cells (56–57). This provides three lines of evidence consistent with a role for shear stress as one mediator of genetic changes induced in the rotating wall vessel.

Differential display of the genes activated and deactivated under rotating wall vessel culture conditions showed rotating wall vessel culture was associated with decreased expression of manganese dependent superoxide dismutase mRNA and increased expression of interleukin-1 b gene mRNA. This greatly extends and brings together previous observations on the interactions of stress, manganese dependent superoxide dismutase expression and interleukin-1. Topper et al. reported an oppositely directed effect, i.e., differential display of vascular endothelial cells exposed to high stress demonstrates increased manganese dependent superoxide dismutase gene expression (57). Other direct evidence links superoxide dismutase and interleukin-1 as increases in manganese superoxide dismutase levels and decreases in interleukin-1 levels in HT-1080 fibrosarcoma cells (58). In more indirect evidence overexpression of mitochondrial manganese superoxide dismutase promotes the survival of tumor cells exposed to interleukin-1 (59). The present study provides direct evidence that modest shear stress decreases magnesium dependent superoxide dismutase in association with an inverse effect on interleukin-1.

The data here demonstrates internal consistency. The changes in magnesium dependent superoxide dismutase were observed on differential display, confirmed by Northern blot analysis, and matched responses were detected by RT-PCR. Megalin demonstrated matched changes in RT-PCR gene and protein expression. Changes in villin observed by RT-PCR were associated with dramatic reformation of microvilli, in which villin is a major structural protein. Although semi-quantitative RT-PCR is prone to inherent variation due to the massive amplification of signals, the use of multiple controls which remain unchanged (b-actin, GAPDH and 18S), and experimental confirmation that reactions were linearly related to cDNA concentration, minimizes these problems. The internally consistent findings by other methods strongly suggests this RT-PCR data is valid.

Study of the mechanisms of action of the rotating wall vessel to induce gene and protein expression during cell culture has been hampered by nomenclature. First, the attachment of the moniker "simulated microgravity", based on engineering analysis of boundary conditions, clouds intuitive analysis of the cell biology as there is no cellular equivalent for this term (1, 6–7). Similarly, the reduced shear stress in the rotating wall vessel compared to stirred fermentors leads to the term "reduced shear stress culture" (1), whereas there is increased shear stress compared to conventional 2-dimensional culture (1, 5). As cell aggregates remain suspended in the rotating wall culture vessels, gravity is balanced by an equal and opposite force. Engineering arguments on the relative contributions of fluid shear, drag, centrifugal force, Coriolis motion, and tangential gravity-induced sedimentation are themselves tangential to the cell biology. Several lines of evidence are documented to indicate that shear stress responses are one of the components of the biological response. This research opens the door for analysis of other biological response mediators in the vessels and for investigation as to whether unloading of gravity plays as big a role as the oppositely directed balancing forces.

Using the rotating wall vessel as a tool, data here provide the first evidence that shear stress response elements, which modulate gene expression in endothelial cells, are also active in epithelial cells, although other investigators failed to see an effect of shear stress on epithelial cells. The present invention demonstrates that epithelial cells have shear stress response elements and change gene expression in response to physical forces including but not limited to sedimentational shear stress. As the rotating wall vessel gains popularity as a clinical tool to produce hormonal implants it is desirable to understand mechanisms by which it induces genetic changes (10, 60), if necessary to prolong the useful life of implants. Several lines of evidence are provided that shear stress response elements are the first mechanism identified by which the rotating wall vessel induces genetic changes. Using a putative endothelial cell shear stress response element binding site as a decoy, the role of this sequence in the regulation of selected genes in epithelial cells was validated. However, many of the changes observed in the rotating wall vessel are independent of this response element. It remains to define other genetic response elements modulated during rotating wall vessel culture, and whether the induced changes are secondary to the balancing forces, or primarily related to unloading gravity.

The following references were cited herein.
1. GOODWIN T J, et al., J cell Biochem 51:301–311, 1993.
2. JESSUP J M, et al., J Cell Biochein 51:290–300, 1993.
3. CHEN T C, et al., In Vitro Cell & Dev Biol 25:714–722, 1989
4. SPAULDING G F, et al., J Cell Biochem 51:249–251, 1993.
5. Kleis S J, et al., Biotech. & Bioeng. 36:771–777, 1990.
6. Wolf D A et al., NASA Technical Paper 3200, 1992.
7. Zhau H E, et al., In Vitro Cell Dev Biol 33:375–380, 19978.
8. Baker T L, et al., In Vitro Cell Dev Biol 33:358–365, 1997
9. Hammond T G, et al., J. Mem. Biol. In press
10. Soon-Shiong P., et al., PNAS USA 90:5843–5847, 1993
11. FREED L E, et al., J cell Biochem 51:257–264, 1993.
12. GOODMAN S, et al., In Hayat M A ed. Colloidal gold principles, methods and applications. Vol 3, New York, Academic Press 1990.
13. GRANT, D. S., et al., In Vitro Cell Dev Biol 27A, 327–336, 1991.
14. Goodwin et al., U.S. Pat. No. 5,496,722, 1996.
15. Wolf et al., U.S. Pat. No. 5,155,034, 1992.
16. Goodwin et al., U.S. Pat. No. 5,153,132, 1992.
17. DeLuca H F., et al., Endocrinology 130(4):1763, 1992
18. Sanjeevkumar C H H, et al., Kidney International. 46:605–612, 1994.
19. DeLuca H F., et al., Ann NY Acad Sci 669:59–68, 1992.
20. Baran D T., et al., J Cell Biochem 56(3):303–6, 1994.
21. Holick M F., et al., Bone 17(2S):107S-111S, 1995.
22. Dechant K L, et al., Drugs & Aging. 5(4):300–317, 1994.
23. Hollis B W., et al., PNAS USA 87:6009–6013, 1990
24. Reinhardt T A, et al., J Clin Endocrinol Metab 58:91–98, 1984.
25. Hollis B W., et al., Clin Chem 32:2060–2063, 1986.
26. Hollis B W, et al., Clin Chem 42:586–592, 1996.
27. Hollis B W, et al., Endocrinology 125(3):1254–1230, 1989.
28. Henry H L. et al., J Biol Chem 254:2722–2729, 1979.
29. Dusso A., et al., Seminars in nephrology. 14(2):144–155, 1994.
30. Gallieni M, et al., Am J Physiol 268(4):F746–F753, 1995.
31. LANGERR., et al., Science 260:920–926, 1993.
32. HEIDRICH H G, et al., J Cell Biol 74:780–789, 1977
33. KEMPSON S A, et al., J Lab Clin Med 113:285–296, 1989
34. TAUB M L, et al., In Vitro Cell & Dev Biol 25:770–775, 1989

35. VANDEWALLE A., et al., J Cell Physiol 141:203–221, 1989
36. VIINAY P, et al., Am J Physiol 241:F403–F411, 1981
37. WILSON P D, et al., Am J Physiol 248:F436–F443, 1985
38. YANG A H, et al. In Vitro Cell & Dev Biol 23:34–46, 1987
39. CHRISTENSEN E I, et al., Sem. in Nephrol. 11(4): 414–439, 1991.
40. MAUNSBACH A B., J. Ultrastruct. Res. 16:1–12,1966.
41. RONCO P, et al., J. Immunol. 136:125–130,1986.
42. SAHALI D, et al., J Exp Med 167:213–218, 1988.
43. SAHALI D, et al., Am J Pathol 142:1654–1667,1993.
44. Hammond, T. G. et al., Kidney Int 42:997–1005, 1992.
45. Schwarz, R. P., et al., J. Tiss. Cult. Meth. 14:51–58, 1992.
46. Topper J N, et al., J. Vasc Res 33:S100A.
47. Hammond, T. G., et al., Cytometry 14: 411–420, 1993.
48. Moestrup, et al., Journal of Clinical Invest, 96:1404–1413, 1995.
49. Schlingensiepen, R., (1997) in Antisense-From Technology to Therapy eds. Schlingensiepen, et al., (Blackwell Science) pp. 1–87.
50. Lennon, G. G., et al., Genomics 33:151–152, 1996.
51. Christensen E I, et al., JASN 8:59A, 1997.
52. Seetharam B. et al., J Clin Invest. 99, 2317–22,1997
53. Orlando R A, et al., PNAS USA 90:4082–4086, 1993.
54. Arpin M, et al., J Cell Biol 107:1759–1.766, 1988.
55. Chantret I, et al., Cancer Res. 48:1936–1942, 1988.
56. Resnick N et al., FASEB J. 9:874–882, 1995.
57. Tuttle Ret al., Curr. Opin. Cell Biol. 3: 70–72, 1993.
58. Melendez J A, et al., J Biol Chem 271(31):18898–18903, 1996.
59. Hibose K, et al., FASEB J 7:361–368, 1993.
60. Soon-Shiong P, et al., The Lancet 343:950–951, 1994.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of increasing 1-α-hydroxylase expression in renal cells comprising:
   isolating human embryonic renal cells; and
   culturing said human embryonic renal cells in a rotating wall vessel containing culture media and a cell culture matrix, wherein gravity is balanced in said rotating wall vessel by oppositely directed physical forces.

2. The method of claim 1, wherein said cell culture matrix comprises micro-carrier beads.

3. The method of claim 1, wherein said renal cells are suitable for therapeutic use.

4. The method of claim 1, wherein said renal cells are suitable for diagnostic use.

5. The method of claim 1, wherein said physical forces comprise sedimentational shear stress.

6. The method of claim 1, wherein said physical forces comprise sedimentational shear stress and centrifugal forces.

7. The method of claim 1, wherein said physical forces comprise viscosity and Coriolis forces.

* * * * *

SEQUENCE LISTING (1) GENERAL INFORMATION:

(iii) NUMBER OF SEQUENCES: 1

(2) INFORMATION FOR SEQ ID NO: 1

(i) SEQUENCE CHARACTERISTICS:
      (A) LENGTH: 22 bp
      (B) TYPE: nucleic acid
      (C) STRANDEDNESS: single-stranded
      (D) TOPOLOGY: linear (ii) MOLECULE TYPE: <Unknown>
      (A) DESCRIPTION: cDNA to mRNA (iii) HYPOTHETICAL: no (iv) ANTI-SENSE: yes (v) FRAGMENT TYPE: <Unknown>

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO: 1:

CTGAGACCGA TATCGGTCTC AG      22